US012087429B2

(12) United States Patent
Orr et al.

(10) Patent No.: US 12,087,429 B2
(45) Date of Patent: Sep. 10, 2024

(54) SURGICAL PLANNING SYSTEMS THAT AUTOMATICALLY ASSESS DIFFERENT POTENTIAL TRAJECTORY PATHS AND IDENTIFY CANDIDATE TRAJECTORIES FOR SURGICAL SYSTEMS

(71) Applicant: ClearPoint Neuro, Inc., Irvine, CA (US)

(72) Inventors: Timothy Neil Orr, Vaughan (CA); Philip Bradley Hotte, Mississauga (CA); Christian Richard Osswald, Elk Grove Village, IL (US)

(73) Assignee: ClearPoint Neuro, Inc., Solana Beach, CA (US)

( * ) Notice: Subject to any disclaimer, the term of this patent is extended or adjusted under 35 U.S.C. 154(b) by 797 days.

(21) Appl. No.: 17/232,429

(22) Filed: Apr. 16, 2021

(65) Prior Publication Data
US 2021/0343397 A1    Nov. 4, 2021

Related U.S. Application Data

(60) Provisional application No. 63/018,215, filed on Apr. 30, 2020.

(51) Int. Cl.
*G16H 30/40*    (2018.01)
*A61B 34/10*    (2016.01)
(Continued)

(52) U.S. Cl.
CPC .............. *G16H 30/40* (2018.01); *A61B 34/10* (2016.02); *A61B 90/11* (2016.02); *G06T 7/11* (2017.01);
(Continued)

(58) Field of Classification Search
CPC ........ G16H 20/40; G16H 30/20; G16H 30/40; G16H 40/67; A61B 34/10; A61B 90/11;
(Continued)

(56) References Cited

U.S. PATENT DOCUMENTS 6,050,992 A    4/2000   Nichols
6,167,311 A    12/2000  Rezai
(Continued)

FOREIGN PATENT DOCUMENTS

WO        0176500 A1       10/2001
WO    2012154961 A2        11/2012
(Continued)

OTHER PUBLICATIONS

Sparks et al., "Anatomy-driven multiple trajectory planning (ADMTP) of intracranial electrodes for epilepsy surgery", Int J CARS (2017) 12, pp. 1245-1255 (Year: 2017).*

(Continued)

*Primary Examiner* — Ping Y Hsieh
*Assistant Examiner* — Jose M Torres
(74) *Attorney, Agent, or Firm* — Myers Bigel, P.A.

(57) ABSTRACT

Surgical planning systems that automatically identify one or a plurality of different candidate trajectories to a defined intrabody treatment region. The systems can rank the identified candidate trajectories in an order of hierarchy based on defined parameters such as distance from a critical no-go location and whether a single or multiple different candidate trajectories are needed to provide coverage of the defined intrabody treatment region. The surgical planning systems are also configured to provide a User Interface that defines a workflow for an image-guided surgical procedure and allows a user to select one or more of the identified candidate trajectories steps in the workflow.

19 Claims, 15 Drawing Sheets

(51) Int. Cl.
*A61B 90/11* (2016.01)
*G06T 7/11* (2017.01)
*G16H 20/40* (2018.01)

(52) U.S. Cl.
CPC ........ *G16H 20/40* (2018.01); *A61B 2034/105* (2016.02); *A61B 2034/107* (2016.02); *G06T 2207/30016* (2013.01)

(58) Field of Classification Search
CPC ........ A61B 2034/104; A61B 2034/105; A61B 2034/107; A61B 2090/363; A61B 2090/3933; G06T 7/11; G06T 2207/30016
See application file for complete search history.

(56) References Cited

U.S. PATENT DOCUMENTS

| | | | |
|---|---|---|---|
| 6,184,521 B1 | 2/2001 | Coffin et al. | |
| 6,198,285 B1 | 3/2001 | Kormos et al. | |
| 6,356,786 B1 | 3/2002 | Rezai et al. | |
| 6,400,155 B2 | 6/2002 | Kormos et al. | |
| 6,405,079 B1 | 6/2002 | Ansarinia | |
| 6,438,423 B1 | 8/2002 | Rezai et al. | |
| 6,483,719 B1 | 11/2002 | Bachman | |
| 6,526,318 B1 | 2/2003 | Ansarinia | |
| 6,539,263 B1 | 3/2003 | Schiff et al. | |
| 6,600,479 B1 | 7/2003 | Smith et al. | |
| 6,609,030 B1 | 8/2003 | Rezai et al. | |
| 6,708,064 B2 | 3/2004 | Rezai | |
| 7,039,266 B1 | 5/2006 | Doty | |
| 7,189,103 B1 | 3/2007 | Brown et al. | |
| 7,283,860 B2 | 10/2007 | Frazier et al. | |
| 7,501,824 B2 | 3/2009 | Kawachi et al. | |
| 8,175,677 B2 | 5/2012 | Sayler et al. | |
| 8,195,272 B2 | 6/2012 | Piferi et al. | |
| 8,208,993 B2 | 6/2012 | Piferi et al. | |
| 8,214,012 B2 | 7/2012 | Zuccolotto et al. | |
| 8,315,689 B2 | 11/2012 | Jenkins et al. | |
| 8,374,677 B2 | 2/2013 | Piferi et al. | |
| 8,509,876 B2 | 8/2013 | Karmarkar | |
| 9,002,076 B2* | 4/2015 | Khadem ................ | A61B 34/20 382/128 |
| 9,042,958 B2 | 5/2015 | Karmarkar et al. | |
| 9,050,470 B2 | 6/2015 | Carlton et al. | |
| 9,136,778 B2 | 9/2015 | Petrenko et al. | |
| 9,498,290 B2 | 11/2016 | Piferi et al. | |
| 9,610,048 B2 | 4/2017 | Vij et al. | |
| 9,844,414 B2 | 12/2017 | Fischer et al. | |
| 10,024,160 B2 | 7/2018 | Stoianovici et al. | |
| 10,105,485 B2 | 10/2018 | Piferi et al. | |
| 10,265,531 B2 | 4/2019 | Bokil | |
| 10,595,744 B2 | 3/2020 | Sayler et al. | |
| 10,905,498 B2 | 2/2021 | Birenbaum et al. | |
| 2001/0053879 A1 | 12/2001 | Mills et al. | |
| 2002/0063688 A1 | 5/2002 | Shaw et al. | |
| 2002/0063935 A1 | 5/2002 | Price et al. | |
| 2004/0030233 A1 | 2/2004 | Frazier et al. | |
| 2005/0273000 A1 | 12/2005 | Dinehart et al. | |
| 2006/0094286 A1 | 5/2006 | Lee et al. | |
| 2007/0002020 A1 | 1/2007 | Ranta et al. | |
| 2007/0152966 A1 | 7/2007 | Krah et al. | |
| 2007/0244387 A1* | 10/2007 | Rodriguez Ponce ... | G16Z 99/00 600/411 |
| 2007/0249911 A1 | 10/2007 | Simon | |
| 2007/0255291 A1 | 11/2007 | Brock et al. | |
| 2008/0097187 A1* | 4/2008 | Gielen ................ | G06T 7/0012 600/409 |
| 2008/0122791 A1 | 5/2008 | Hsu | |
| 2008/0123922 A1 | 5/2008 | Gielen et al. | |
| 2008/0306375 A1 | 12/2008 | Sayler et al. | |
| 2009/0093705 A1 | 4/2009 | Vangdal | |
| 2009/0171184 A1 | 7/2009 | Jenkins et al. | |
| 2009/0177077 A1 | 7/2009 | Piferi et al. | |
| 2009/0189988 A1 | 7/2009 | Qu et al. | |
| 2009/0195514 A1 | 8/2009 | Glynn et al. | |
| 2009/0196621 A1 | 8/2009 | Chen | |
| 2009/0234218 A1 | 9/2009 | Washburn et al. | |
| 2010/0150572 A1 | 6/2010 | Lee et al. | |
| 2010/0312096 A1 | 12/2010 | Guttman et al. | |
| 2011/0208980 A1 | 8/2011 | Brooks et al. | |
| 2011/0234497 A1 | 9/2011 | Zahnert et al. | |
| 2012/0013525 A1 | 1/2012 | Trcka et al. | |
| 2012/0319975 A1 | 12/2012 | Fuchs et al. | |
| 2013/0162510 A1 | 6/2013 | Ohgishi et al. | |
| 2013/0172906 A1 | 7/2013 | Olson et al. | |
| 2013/0182085 A1 | 7/2013 | Ziarati | |
| 2013/0333477 A1 | 12/2013 | Kataoka | |
| 2014/0003696 A1* | 1/2014 | Taghva ................. | G06T 7/0012 382/131 |
| 2014/0244880 A1 | 8/2014 | Soffer | |
| 2016/0051187 A1 | 2/2016 | Damadian | |
| 2016/0065912 A1 | 3/2016 | Peterson | |
| 2017/0000567 A1* | 1/2017 | Kim .................... | A61B 10/0233 |
| 2017/0367776 A1 | 12/2017 | Kwok et al. | |
| 2019/0209245 A1* | 7/2019 | Sparks ................. | G06T 19/003 |
| 2019/0336232 A1* | 11/2019 | Jenkins ................ | A61B 34/74 |
| 2021/0121236 A1* | 4/2021 | Varkuti ................ | A61B 34/25 |

FOREIGN PATENT DOCUMENTS

| | | |
|---|---|---|
| WO | 2014003855 A1 | 1/2014 |
| WO | 2017181150 A1 | 10/2017 |
| WO | 2018038608 A1 | 3/2018 |

OTHER PUBLICATIONS

Sparks et al., "Automated multiple trajectory planning algorithm for the placement of stereo-electroencephalography (SEEG) electrodes in epilepsy treatment", Int J Cars (2017) 12, pp. 123-136 (Year: 2017).*

"NeuroQuant" From URL: https://www.cortechslabs.com/products/neuroquant/, Accessed On: Apr. 30, 2020 (10 pages).

"WayPoint™ Navigator Software" From URL: https://www.fh-co.com/product/waypoint-navigator-software, Accessed on: Apr. 30, 2020 (4 pages).

Data Sheet for Optical USB Extension Cable, Opticis (5 pages) (Jan. 21, 2008).

Dembek et. al. "Directional DBS leads show large deviations from their intended implantation orientation" Parkinsonism & related disorders 67:117-121 (2019).

Dembek et. al. "Probabilistic mapping of deep brain stimulation effects in essential tremor" NeuroImage: Clinical 13:164-173 (2017).

Dodin et al. "A fully automated human knee 3D MRI bone segmentation using the ray casting technique" Medical & Biological Engineering & Computing 49(12):1413-1424 (Dec. 2011).

Eisenstein et. al. "Functional anatomy of subthalamic nucleus stimulation in Parkinson disease" Annals of neurology 76(2):279-295 (2014).

Garcia-Garcia et. al. "Stimulation sites in the subthalamic nucleus and clinical improvement in Parkinson's disease: a new approach for active contact localization" Journal of neurosurgery 125(5):1068-1079 (2016).

Hellerbach et. al. "DiODe: directional orientation detection of segmented deep brain stimulation leads: a sequential algorithm based on CT imaging" Stereotactic and functional neurosurgery 96(5):335-341 (2018).

Horn et. al. "Connectivity predicts deep brain stimulation outcome in Parkinson disease" Annals of neurology 82(1):67-78 (2017).

Kronman et al. "Anatomical Structures Segmentation by Spherical 3D Ray Casting and Gradient Domain Editing" Medical Image Computing and Computer-Assisted Intervention—MICCAI 2012. MICCAI 2012, Lecture Notes in Computer Science 7511:363-370 (2012).

Mosley et. al. "The site of stimulation moderates neuropsychiatric symptoms after subthalamic deep brain stimulation for Parkinson's disease" NeuroImage: Clinical 18:996-1006 (2018).

U.S. Appl. No. 17/185,060, filed Feb. 25, 2021.
U.S. Appl. No. 62/988,609, filed Mar. 12, 2020.

(56) References Cited

OTHER PUBLICATIONS

Weese et al. "Shape-Constrained Deformable Models and Applications in Medical Imaging" Shape Analysis in Medical Image Analysis, Lecture Notes in Computational Vision and Biomechanics 14:151-184 (2014).
International Search Report and the Written Opinion of the International Searching Authority corresponding to International Patent Application No. PCT/US2021/027713 (16 pages) (mailed Aug. 12, 2021).
Cole et al. "Design of a Robotic System for MRI-Guided Deep Brain Stimulation Electrode Placement" IEEE International Conference on Robotics and Automation, 4450-4456 (2009).
Wang et al. "MRI Compatibility Evaluation of a Piezoelectric Actuator System for a Neural Interventional Robot" 31st Annual International Conference of the IEEE EMBS, 6072-6075 (2009).

\* cited by examiner

US 12,087,429 B2

SURGICAL PLANNING SYSTEMS THAT AUTOMATICALLY ASSESS DIFFERENT POTENTIAL TRAJECTORY PATHS AND IDENTIFY CANDIDATE TRAJECTORIES FOR SURGICAL SYSTEMS

RELATED APPLICATIONS

This patent application claims the benefit of and priority to U.S. Provisional Application Ser. No. 63/018,215 filed Apr. 30, 2020, the content of which is hereby incorporated by reference as if recited in full herein.

FIELD OF THE INVENTION

The present invention relates to surgical planning systems for image-guided interventional systems.

BACKGROUND OF THE INVENTION

Surgical planning prior to intervention can be an important aspect of a surgery, particularly in the field of neurosurgery. However, the selection of appropriate planning trajectory paths, particularly into the brain, can be tedious and time consuming.

There remains a need for methods and systems that can reduce the time required by a physician for identifying a suitable trajectory path to a target interventional site.

SUMMARY

Embodiments of the present invention are directed to surgical planning systems that automatically identify one or more different candidate trajectories (a trajectory path from a location outside the patient body to a target intrabody treatment region) and, if more than one, rank the identified candidate trajectories based on defined parameters.

The defined parameters can include distance from a critical or "no-go" location and whether a single or multiple different candidate trajectories are needed to provide coverage of the target intrabody treatment region(s).

The surgical planning systems can be configured to provide a user interface that defines a workflow for an image-guided surgical procedure and accept user input to select one or more of the identified candidate trajectories steps in the workflow.

Embodiments of the present invention are directed to surgical planning systems. The systems include a workstation with a display and a computer system in communication with or at least partially onboard the workstation. The computer system is configured to: provide at least one image of a brain of a patient; register a digital brain atlas to the at least one image; accept user input to confirm and/or identify at least one target treatment region in the brain of the patient; determine regions in the brain that are to be avoided; and identify one candidate trajectory or a plurality of different candidate trajectories for providing a respective trajectory path from a location external to the patient to the at least one target treatment region as a surgical treatment path.

The identified one or the identified plurality of candidate trajectories can be identified by: dividing a surface of a head of the patient into defined sub-areas that correspond to potential entry sites into the brain; dividing one or more target volumes within the brain into sub-volumes; and for at least some of the defined sub-areas: identifying whether there is a trajectory to one or more sub-volume of the sub-volumes that does not pass through any of the determined regions to be avoided and that extend to at least a portion of the at least one target treatment region whereby, if so, a respective surface sub-area and corresponding sub-volume defines a respective candidate trajectory for the identified one candidate trajectory or the identified plurality of candidate trajectories.

The identified one or the identified plurality of candidate trajectories can be identified by: (virtually) dividing a surface of a head of the patient into defined sub-areas that correspond to potential entry sites into the brain; and for at least some of the defined sub-areas: ray casting to identify virtual rays that do not pass through any of the determined regions to be avoided and that extend to at least a portion of the at least one target treatment region whereby, if so, a respective surface sub-area and corresponding ray to one or more sub-volumes define a respective candidate trajectory for the identified one candidate trajectory or the identified plurality of candidate trajectories.

The system can be configured to electronically (virtually) divide one or more target volumes within the brain into sub-volumes before the ray casting and the ray casting can be carried out to identify whether a virtual (straight linear) ray extending from a respective sub-area to one or more of the sub-volumes does not pass through any of the determined regions to be avoided.

The target volume can be an eroded target volume of the at least one target treatment region that is reduced in volume from an original volume of the at least one target treatment region by a defined treatment radius.

The defined sub-areas can have a defined geometric shape, optionally a square, and can have a maximal length of an outer perimeter side thereof in a range of 0.1 mm-2 mm.

The sub-volumes can be cubic sub-volumes can have a maximal length of an outer perimeter side thereof in a range of about 0.1 mm-2 mm.

The system can be configured to accept user input to either input stereotactic frame parameters of a stereotactic frame or select a stereotactic frame from defined stereotactic frames that will be used during a surgical procedure to identify angulation and entry point regions thereof; define a desired treatment radius of the at least one target treatment region; and identify and/or select a surgical device that will be used to carry out a desired surgical treatment. In response to the identification or selection, the system can be configured to provide corresponding physical parameters including thickness and a length of the identified and/or selected surgical device. The identifying the one or the plurality of candidate trajectories uses the provided physical parameters as computational inputs.

The system can be configured to provide electronically selectable surgical devices including one or more of: an intrabrain fluid delivery device; an intrabrain fluid/tissue withdrawal device; a thermal therapy device; and an implantable electrode(s).

The system can provide user-selectable input parameters of: a plurality of different stereotactic frames, each having an associated electronically defined physical limit of operation for providing adjustable/selectable trajectory paths; and a plurality of different treatment devices that are useable to deliver a surgical treatment via the trajectory path of the one or a selected one or more of the plurality of candidate trajectories. Each treatment device can have associated electronically defined features such as one or more of shape, size, length and/or thickness.

The system can be further configured to accept user input to: edit a volume associated with the at least one target treatment region; and edit determined regions that are to be avoided for the trajectory path.

The system can be configured to identify the plurality of different candidate trajectories and provide the plurality of different candidate trajectories in a ranked order based on defined rules and/or parameters.

The system can be configured to identify the plurality of different candidate trajectories and provide the plurality of different candidate trajectories in a ranked order.

The ranked order can be based, at least in part, on a distance each respective candidate trajectory resides from at least a closest one of the determined regions that are to be avoided.

The system can be configured to identify the plurality of different candidate trajectories and provide the plurality of different candidate trajectories in a ranked order based, at least in part, on whether there is one or more single one of the different candidate trajectories that provides complete coverage inside a treatment radius of the at least one target treatment region.

If there is no single one of the plurality of different candidate trajectories that can provide the complete coverage, the computer system can be configured to provide the plurality of different candidate trajectories in a ranked order, based, at least in part, on whether a single stereotactic frame is able to accommodate at least two of the plurality of different candidate trajectories and provide complete coverage of the at least one target treatment region and a distance each respective candidate trajectory resides from at least a closest one of the determined regions that are to be avoided.

If there is no single one of the different candidate trajectories that can provide the complete coverage and no single stereotactic frame that is able to accommodate the at least two different candidate trajectories to provide the complete coverage, the computer system is configured to provide the plurality of different candidate trajectories in a ranked order, based, at least in part, on two-stereotactic frame solutions having a lesser number of trajectories that provides the complete coverage of the at least one treatment region and based on a distance each respective candidate trajectory resides from at least a closest one of the determined regions that are to be avoided.

The surgical planning system can be configured to electronically control a motor drive system to turn actuators coupled to a trajectory guide that adjust a trajectory of the trajectory guide to provide a selected candidate trajectory from the one identified candidate trajectory or from the plurality of candidate trajectories.

The system can be provided in combination with a CT or MRI scanner. The workstation can be in communication with the CT or MRI scanner and the workstation can have a DICOM interface that receives images from the CT or MRI scanner to provide the at least one image for the surgical planning system.

Other embodiments are directed to methods of identifying a candidate trajectory/trajectories for a trajectory guide held by a stereotactic frame for surgical planning. The methods include: providing or obtaining (e.g., loading) at least one image of a head (and brain) of a patient; electronically registering a digital brain atlas to the at least one image; electronically determining regions in a brain of the head of the patient that are to be avoided; electronically dividing a surface of the head of the patient into defined sub-areas that correspond to potential entry sites into the brain; and electronically identifying one candidate trajectory or a plurality of candidate trajectories for providing a respective trajectory path from a location external to the patient to the at least one target treatment region as a surgical treatment path.

The identifying can include, for at least some of the defined sub-areas, one or more of: identifying a trajectory that does not pass through any of the determined regions to be avoided and that extend to at least a portion of the at least one target treatment region as the one or the plurality of candidate trajectories; and/or ray casting virtual rays that extend from a respective sub-area to at least one target treatment region and that does not pass through any of the determined regions to be avoided as the one or the plurality of candidate trajectories.

The target volume can be an eroded target volume of the at least one target treatment region that is reduced in volume from an original volume of the at least one target treatment region by a defined treatment radius.

The defined sub-areas can have a defined geometric shape, optionally a square. The shape can have a maximal side length in a range of 0.1 mm-2 mm. The sub-volumes can be cubic sub-volumes with a maximal side length in a range of 0.1 mm-2 mm.

The method can further include, before or after defining the sub-volumes, for at least some of the surface sub-areas, optionally for each, calculating geometric shapes of reachable trajectories allowed by parameters of a selected or defined stereotactic frame.

The electronically identifying can be carried out to identify the plurality of different candidate trajectories and the method can further include providing the plurality of different candidate trajectories in a ranked order based on defined rules and/or parameters.

The electronically identifying can be carried out to identify the plurality of different candidate trajectories and the method can further include providing the plurality of different candidate trajectories in a ranked order based, at least in part, on a distance each respective candidate trajectory resides from at least a closest one of the determined regions that are to be avoided.

The electronically identifying can be carried out to identify the plurality of different candidate trajectories and the method can further include providing the plurality of different candidate trajectories in a ranked order based, at least in part, on whether there is one or more single one of the different candidate trajectories that provides complete coverage inside a treatment radius of the at least one target treatment region.

If there is no single one of the candidate trajectories that can provide the complete coverage, the method can further include providing the plurality of different candidate trajectories in a ranked order, based, at least in part, on whether a single stereotactic frame is able to accommodate at least two of the plurality of different candidate trajectories and provide complete coverage of the at least one target treatment region, and based on a distance each respective candidate trajectory resides from at least a closest one of the determined regions that are to be avoided.

If there is no single one of the candidate trajectories that can provide the complete coverage and no single stereotactic frame that is able to accommodate the at least two different candidate trajectories to provide the complete coverage, the method can further include providing the plurality of different candidate trajectories in a ranked order, based, at least in part, on two-stereotactic frame solutions having a least number of trajectories to provide the complete coverage and based on a distance each respective candidate trajectory resides from the determined regions that are to be avoided.

Still other embodiments are directed to computer program product for facilitating an image-guided surgical procedure. The computer program product having at least one processor configured to: provide at least one image of a head of a patient; register a digital brain atlas to the at least one image; determine regions in a brain of the head of the patient that are to be avoided; divide a surface of the head of the patient into defined sub-areas that correspond to potential entry sites into the brain; and identify one candidate trajectory or identify a plurality of candidate trajectories.

The identification can be configured to identify for at least some of the defined sub-areas, a trajectory from a respective sub-area that does not pass through any of the determined regions to be avoided and that extends to at least a portion of the at least one target treatment region to define the one candidate trajectory or the plurality of candidate trajectories.

The identification can be configured to ray cast virtual rays with a respective virtual ray that extends from a respective sub-area to at least one target treatment region and that does not pass through any of the determined regions to be avoided as one candidate trajectory.

The at least one processor can be further configured to divide the target treatment volume of the brain into sub-volumes and the identification of the one or more candidate trajectories can be carried out using a virtual trajectory line extending between a respective sub-volume and sub-area that does not pass through any of the determined regions to be avoided.

These and other embodiments will be described further below.

DETAILED DESCRIPTION

Figure 1:
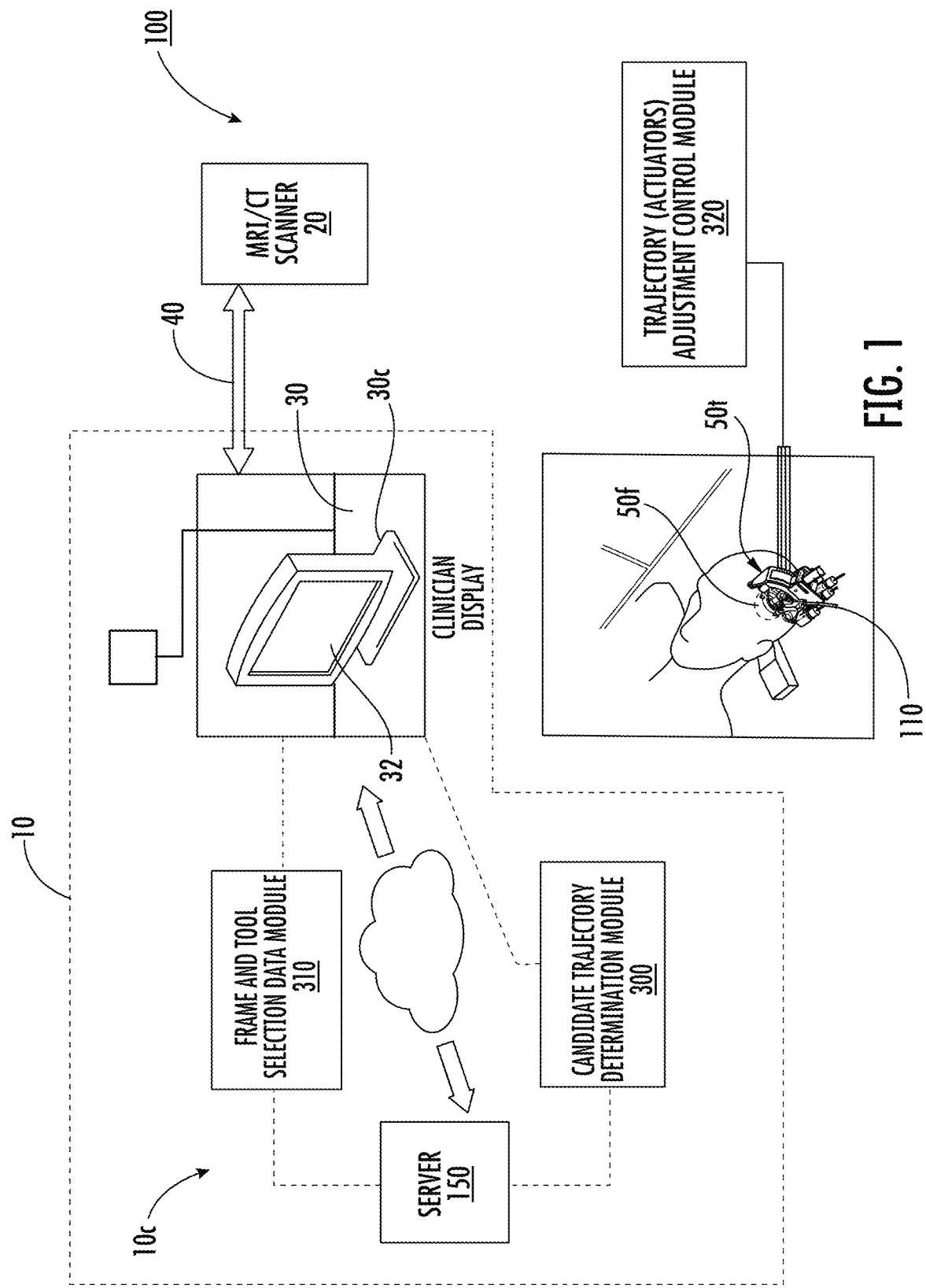
FIG. 1 is a schematic illustration of a surgical system according to some embodiments of the present invention.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. The abbreviation "FIG." may be used interchangeably with "FIG." and the word "Figure" in the specification and figures. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit of flow diagrams) illustrate optional features or operations, unless specified otherwise. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments.

The term "computer system" refers to any computer system and can include one or more processors, databases and servers. The computer system can comprise a local area network (LAN), a wide area network (WAN) and/or the internet. The computer system can comprise and/or be provided as a cloud computing resource. The computer system can comprise software and hardware and can reside at least partially on a workstation of a surgical planning and/or image-guided surgical system.

The term "brain atlas" refers to a digital model of features of a brain, human brain for human uses and animal brains for respective animal uses. The planning system can be independent of any particular atlas. One example brain atlas is the WayPoint™ Navigator Software (manufacturer: FHC) which has an integrated brain atlas to assist with surgical planning and predictive modelling for DBS, LITT and epilepsy procedures. See, https://www.fh.com/product/waypoint-navigator-software. Another example is the NeuroQuant® Software (manufacturer: Cortech Labs) which has an integrated brain atlas to automatically detect 3D anatomical structures from MR scans for purposes of planning and neurological assessment. See, https: https://www.cortechslabs.com/products/neuroquant/#. Both accessed as of Apr. 30, 2020. The contents of the noted websites are hereby incorporated by reference as if recited in full herein. The brain atlas can be linked or referenced rather than included in an onboard library of the surgical planning system.

The term "ACPC coordinate space" refers to a right-handed coordinate system defined by anterior and posterior commissures (AC, PC) and Mid-Sagittal plane points, with positive directions corresponding to a patient's anatomical Right, Anterior and Head directions with origin at the mid-commissure point.

The term "grid" refers to a pattern of crossed lines or shapes used as a reference for locating points or small spaces, e.g., a series of rows and intersecting columns, such as horizontal rows and vertical columns (but orientations other than vertical and horizontal can also be used). The grid can include associated visual indicia such as alphabetical markings (e.g., A-Z and the like) for rows and numbers for columns (e.g., 1-10) or the reverse. Other marking indicia may also be used. The grid can be provided as a flexible patch that can be releasably attached to the skull or scalp of a patient. For additional description of suitable grid devices, see co-pending, co-assigned U.S. patent application Ser. No. 12/236,621, the contents of which are hereby incorporated by reference as if recited in full herein.

The term "fiducial marker" refers to a marker that can be electronically identified using image recognition and/or electronic interrogation of image data. The fiducial marker can be provided in any suitable manner, such as, but not limited to, a geometric shape of a portion of the tool, a component on or in the tool, a coating or fluid-filled component or feature (or combinations of different types of fiducial markers) that, for MRI/CT uses, makes the fiducial marker(s) visible in a respective imaging modality with sufficient signal intensity (brightness) for identifying location and/or orientation information for the tool and/or components thereof in space.

The terms "RF safe" and "MRI compatible" means that the so-called component(s) is safe for use in an MRI environment and as such is typically made of a non-ferromagnetic MRI compatible material(s) suitable to reside and/or operate in a high magnetic field environment, without inducing unplanned current that inadvertently unduly heats local tissue or otherwise interferes with the planned therapy.

The term "high-magnetic field" refers to field strengths above about 0.5 T, typically above 1.0T, and more typically between about 1.5T and 10T, including 3T systems. MRI Scanners are well known and include high-field closed bore and open bore systems.

The term "MRI visible" means that the device is visible, directly or indirectly, in an MRI image. The visibility may be indicated by the increased SNR of the MRI signal proximate the device.

The term "ray casting" is well known to those of skill in the art and refers to electronically casting rays to sample volumetric data sets to solve a variety of problems in computer graphics and computational geometry. The term "point cloud" refers to a volumetric location/space in a 3D image associated with end point portions of rays used to identify whether the ray extends to a desired volumetric space associated with a target treatment region and/or tissue bounding the desired volumetric space. See, by way of example only, Dodin, P., Martel-Pelletier, J., Pelletier, J.-P., Abram, F. (2011) A fully automated human knee 3D MRI bone segmentation using the ray casting technique. Medical & Biological Engineering & Computing, December 2011, Volume 49, Issue 12, pp 1413-1424; and Kronman A., Joskowicz L., Sosna J. (2012) Anatomical Structures Segmentation by Spherical 3D Ray Casting and Gradient Domain Editing. In: Ayache N., Delingette H., Golland P., Mori K. (eds) Medical Image Computing and Computer-Assisted Intervention—MICCAI 2012. MICCAI 2012. Lecture Notes in Computer Science, vol 7511. Springer, Berlin, Heidelberg. The contents of these documents are hereby incorporated by reference as if recited in full herein.

Generally stated, embodiments of the present invention are directed to methods, systems, and computer program products for surgical planning that use defined inputs to automatically identify and provide and/or output candidate trajectories from a location external to a patient to a target intrabody treatment region(s) and/or volume(s). The methods, systems and computer program products can reduce the time required by a surgeon to carry out surgical planning to select a trajectory used during a clinical procedure. The candidate trajectories can be used (on the day of surgery) to select one or more viable trajectory paths for a clinical procedure such a placing a surgical device at a target treatment volume(s) for intervention/treatment. Thus, the time spent by a surgeon can be reduced by partially or substantially totally automating the candidate trajectory determination procedure.

In particular embodiments, the systems define and present workflow with discrete steps for finding candidate trajectories from an entry point(s), optionally then guiding the alignment of the targeting cannula to a selected one or more of the candidate trajectories, monitoring the insertion of the device into the brain, and adjusting the trajectory guide to provide the desired trajectory path in cases where the placement needs to be corrected.

Embodiments of the present invention will now be described in further detail below with reference to the figures. FIG. 1 illustrates a surgical planning system 10 that may optionally be provided as part of an image-guided interventional system 100. The surgical planning system 10 comprises a computer system 10c and can comprise or communicate with a clinician workstation 30 and at least one display 32. The computer system 10c can comprise at least one data processing circuit 30c.

The surgical planning system 10 can include a candidate trajectory determination module 300 and a support frame and tool selection module 310. The support frame and tool selection module 310 comprises physical data of actual surgical devices 50 for computational uses in determining suitable trajectory paths for the devices, when used. The candidate trajectory determination module 300 can be configured to use the physical data provided by the support frame and tool selection module to define suitable candidate trajectories as will be discussed further below. The support frame 50f can be one or more commercially available stereotactic frames and/or trajectory guides 50t with known limits of angulation with respect to an entry site, for example. The actual surgical devices 50 can include fluid transfer devices such as pharmaceutical delivery devices, ablation probes, stimulation electrodes and the like. The actual surgical devices 50 can be configured as one or more of: an intrabrain fluid delivery device; an intrabrain fluid/tissue withdrawal device; a thermal therapy device such as, but not limited to, an ablation device, a hyperthermia device and a hypothermia device; and an implantable electrode(s).

Where the surgical planning system 10 communicates with and/or is provided as part of the image-guided interventional system 100, the workstation 30 can communicate with a scanner 20, such as an MRI and/or CT scanner via an interface 40 that may be used to allow communication between the workstation 30 and the scanner 20. The interface 40 and/or circuit 30c may be hardware, software or a combination of same. The interface 40 and/or circuit 30c may reside partially or totally in the scanner 20, partially or totally in the workstation 30, or partially or totally in a discrete device therebetween.

The workstation 30 and/or circuit 30c can passively or actively communicate with the scanner 20. The system can also be configured to use functional patient data (e.g., fiber tracks, fMRI and the like) to help plan or refine a target surgical site. See, e.g., U.S. Pat. No. 8,315,689 for additional information on example workflows and surgical systems, the contents of which are hereby incorporated by reference as if recited in full herein.

Still referring to FIG. 1, the surgical planning system 10 can comprise a server 150 as part of the computer system 10c that can provide and/or be in communication with the candidate trajectory determination module 300 and/or the frame and tool selection data module 310. The workstation 30 can communicate with the server 150 via a computer network, such as one or more of local area networks (LAN), wide area networks (WAN) and can include a private intranet and/or the public internet (also known as the World Wide Web or "the web" or "the internet"). The server 150 can include and/or be in communication with the modules 300, 310 using appropriate firewalls for HIPAA (Health Insurance Portability Accountability Act) or other regulatory compliance.

The computer system 10c and/or server 150 can be provided using cloud computing which includes the provision of computational resources on demand via a computer network. The resources can be embodied as various infrastructure services (e.g., compute, storage, etc.) as well as applications, databases, file services, email, etc. In the traditional model of computing, both data and software are typically fully contained on the user's computer; in cloud computing, the user's computer may contain little software or data (perhaps an operating system and/or web browser) and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers.

The image-guided systems 100 can be configured to carry out diagnostic and interventional procedures such as to guide and/or place interventional devices to any desired internal region of the body or object but may be particularly suitable for neurosurgeries. The object can be any object and may be particularly suitable for animal and/or human subjects. For example, the system can be used for gene and/or stem-cell based therapy delivery or other neural therapy delivery and allow user-defined custom targets in the brain or to other locations. In addition, embodiments of the systems can be used to thermally treat tissue (e.g., ablate, provide hyperthermia, provide hypothermia and/or provide combinations of same) in the brain or other locations and/or place electrode stimulation leads. In some embodiments, it is contemplated that the systems can be configured to treat AFIB in cardiac tissue, and/or to deliver stem cells or other cardio-rebuilding cells or products into cardiac tissue, such as a heart wall, via a minimally invasive MRI guided procedure while the heart is beating (i.e., not requiring a non-beating heart with the patient on a heart-lung machine). In some embodiments, the systems can be used to facilitate cell lysing to stimulate the immune system or other functional body systems.

Examples of known treatments and/or target body regions are described in U.S. Pat. Nos. 6,708,064; 6,438,423; 6,356,786; 6,526,318; 6,405,079; 6,167,311; 6,539,263; 6,609,030 and 6,050,992, the contents of which are hereby incorporated by reference as if recited in full herein.

Figure 5:
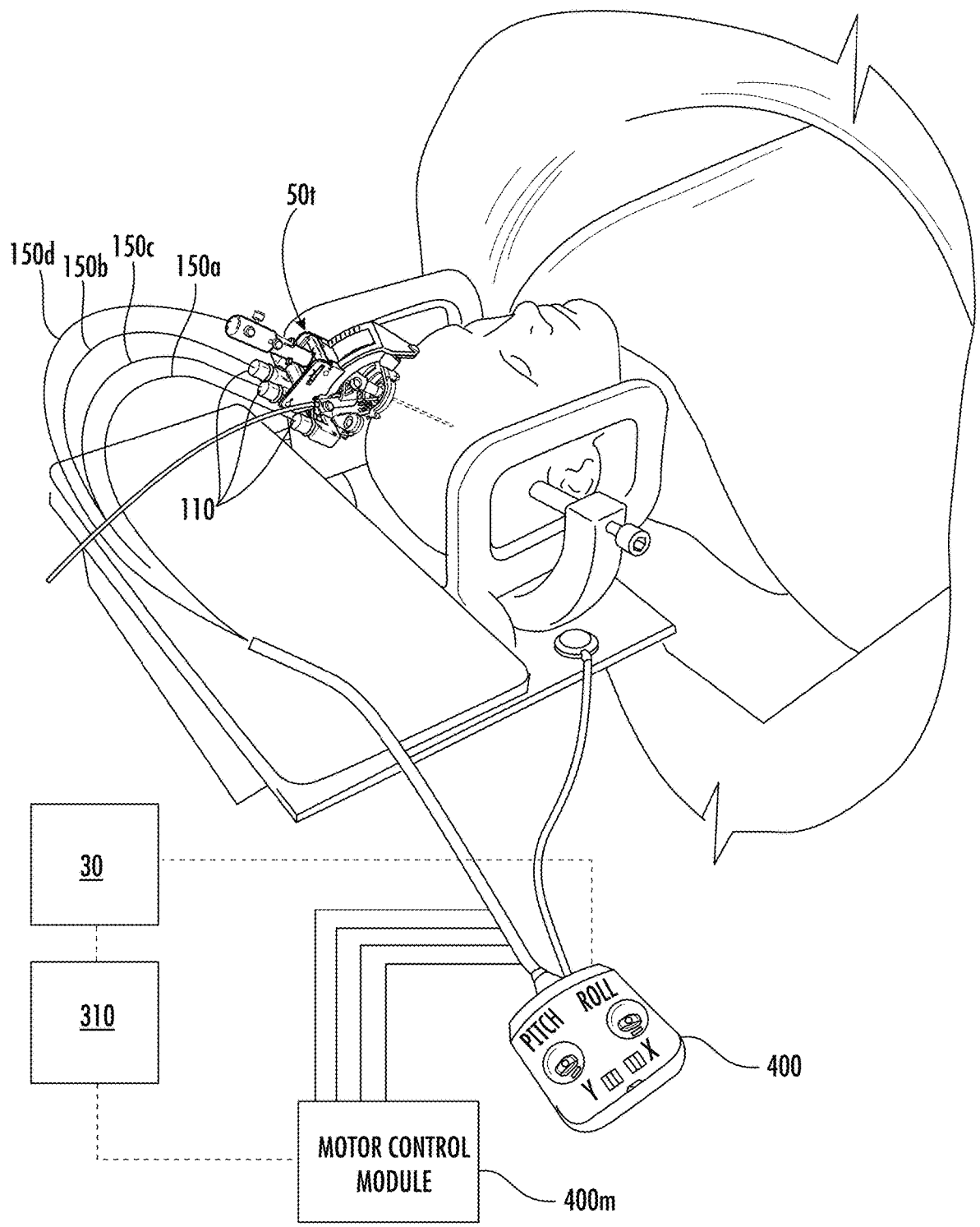
FIG. 5 is a schematic illustration of an example surgical system with an actuator control module that is in communication with the candidate trajectory identification module that can be used to adjust a trajectory guide to use a selected one or more of the candidate trajectories to carry out a surgical intervention according to embodiments of the present invention.

Still referring to FIG. 1, the image-guided surgical system 100 can include a trajectory adjustment control module 320 that can be used to automatically move actuators 110 of the trajectory guide 50t or provide movement directions for a user to manually move the actuators 110 desired amounts to provide a selected candidate trajectory identified by the candidate trajectory determination module 300. FIG. 5 illustrates that the image-guided surgical system 100 can have either a manual user input 400 or an automated motor control module 400m, each or only one of which can be connected to a plurality of actuators 110, via cables 150a, 150b, 150c and 150d, that move the trajectory guide 50t in defined directions, for example X, Y, pitch and roll directions.

The motor control module 400m can comprise MRI-compatible stepper motors that reside in a housing in an MRI scanner room, optionally coupled to the patient bed so as to be able to move in and out of the bore of the magnet while coupled to the bed. See, e.g., co-pending U.S. Provisional Patent Application Ser. No. 62/988,609, filed Mar. 12, 2020, and U.S. patent application Ser. No. 17/185,060, filed Feb. 25, 2021, the contents of which are hereby incorporated by reference as if recited in full herein.

To be clear, embodiments of the invention can be provided as a separate data processing system and/or module that can identify and output one or more candidate trajectories that can be used on the day of the procedure, optionally with the system 100 and/or motor control module 400m. The data processing system can be compatible with MRI and/or CT systems.

The MRI scanner 20 can include a console that has a "launch" application or portal for allowing communication to the circuit 30c of the workstation 30. The scanner console can acquire volumetric image data of a respective patient, such as, for example, T1-weighted (post-contrast scan) data or other image data (e.g., high resolution image data for a specific volume) of a patient's head and/or brain (or other target anatomy).

In some embodiments, the console can push DICOM images or other suitable image data to the workstation 30 and/or circuit 30c. The workstation 30 and/or circuit 30c can be configured to passively wait for data to be sent from the MR scanner 20 and the circuit 30c/workstation 30 does not query the scanner or initiate a communication to the scanner. In other embodiments, a dynamic or active communication protocol between the circuit 30c/workstation 30 and the scanner 20 may be used to acquire image data and initiate or request particular scans and/or scan volumes. Also, in some embodiments, pre-DICOM, but reconstructed image data, can be sent to the circuit 30c/workstation 30 for processing or display. In other embodiments, pre-reconstruction image data (e.g., substantially "raw" image data) can be sent to the circuit 30c/workstation 30 for processing, optionally for Fourier Transform reconstruction and/or for AI (artificial intelligence, machine learning) reconstruction.

Embodiments of the invention are particularly useful for neurosurgeries such as deep brain surgeries. The surgical planning system 10 can be configured to analyze obtained patient images, define volumes of interest in the brain, define virtual geometric shapes of trajectories that can be provided by a stereotactic frame or frames 50f or other parameters thereof to be used during surgery, as well as physical characteristics of the surgical devices 50 to be inserted into the brain to automatically compute candidate trajectory paths for neurosurgical planning purposes.

An end user, such as a neurosurgeon, can prepare, review and finalize inputs using a defined workflow. Once the inputs are provided, (and also typically prepared and reviewed by a user), a defined set of rules can automatically determine a list of candidate trajectories (intra-body trajectory paths) that can be presented to the user, typically via a display of a computer system such as a clinician workstation.

The methods, systems, and computer program products can be configured to review the list of candidate trajectories and rank, optionally select and serially or concurrently, present to a display 32, one or more that can be used during the clinical procedure.

The list of candidate trajectories can be ranked based on defined rules to provide the list in a ranked order of preference. The ranking can be from high to low or low to high to indicate the candidate trajectory that is most likely to be optimal or preferred to least likely to be optimal or preferred.

The defined rules can rank the candidate trajectories relative to one another. The defined rules can include a rule that considers whether a candidate trajectory is further away (maximizing distance) from a known "no-go" location as preferential to other candidate trajectories that are closer to a known "no-go" location. The defined rules can rank a candidate trajectory that only requires a single trajectory path to totally cover the defined treatment volume(s) higher than candidate trajectories that do not cover the entire defined treatment volume so as to require more than one candidate trajectory to cover the defined treatment volume (s) to thereby minimize the number of different candidate trajectories used during a surgical procedure.

The defined rules may also be implemented to use other or additional criteria to rank the candidate trajectories as appropriate.

The planning system 10 can be configured to have a specific set of system inputs that can be used to determine the candidate planned trajectories, including magnetic resonance and/or computed tomography patient scans, regions within the brain that are targeted (i.e. "target regions"), areas within the brain that should be avoided (i.e. "no go regions"), a radius of a required treatment area, angulation characteristics of one or more stereotactic frame(s) 50f that will be used during the procedure, and physical characteristics (length, diameter) of surgical device(s) 50 that will be inserted into the brain during the procedure.

The planning system 10 can be configured to provide a customized workflow which allows the user to select/prepare, review and validate that all required inputs for the computer assisted method of identifying candidate trajectories are appropriate, and that the outputted candidate trajectories are anatomically viable. The planning system 10 can be configured to execute the workflow and allow/require validation of inputs and outputs and can automatically identify target treatment regions/structures and/or avoidable structures utilizing an integrated or linked digital brain atlas. The planning system 10 can be configured to automatically identify and/or determine candidate trajectories and allow final review/selection. The planning system 10 can export the one or more selected candidate trajectories for use during a respective clinical procedure.

Figure 2:
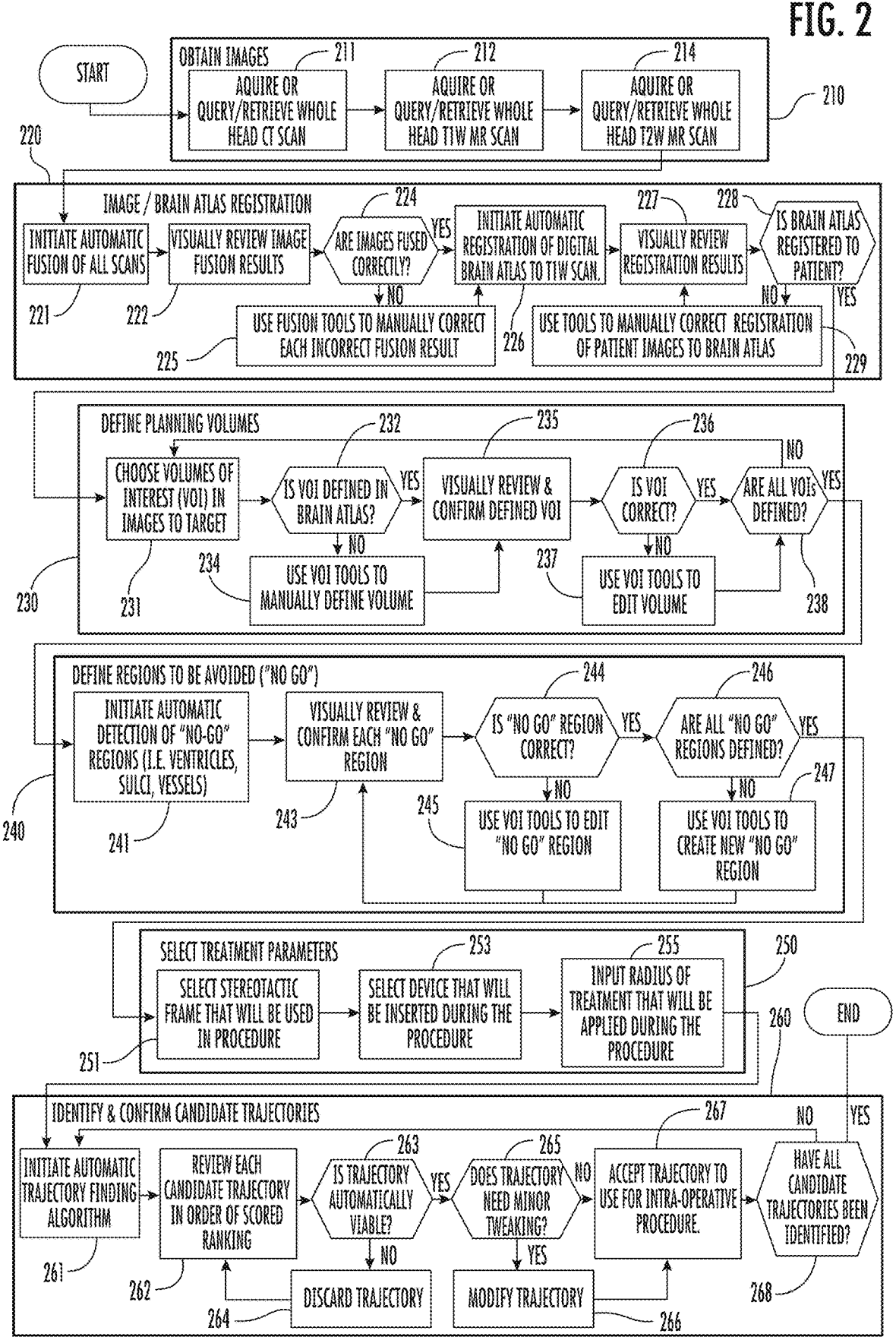
FIG. 2 is a flow chart of example actions that can be carried out by an automated/semi-automated surgical planning system according to embodiments of the present invention.

For example, referring to FIG. 2, an example of a flow chart of actions of a surgical planning system 10 is shown that can automatically identify potential candidate entry and target point combinations based on defined and/or specified inputs. As shown, at least one patient image is obtained (block 210); the obtained at least one image is registered to a brain atlas (block 220); then planning volumes are defined (block 230); and regions to be avoided ("NO GO" regions) are identified/defined (block 240); treatment parameters are selected (block 250); and candidate trajectories are identified and selected/confirmed (block 260).

The at least one obtained image can be carried out to acquire or query/retrieve a whole head CT scan (block 211), and a whole head T1W MR scan (block 212) and a whole head T2W MR scan (block 214).

The registration can be carried out by initiating automatic fusion of all scans (block 221) and allow/prompt a user to visually review image fusion results (block 222).

Are images fused correctly? (block 224). If (No), fusion tools can be used to allow a user to manually correct each incorrect fusion result (block 225). If (Yes), automatic registration of digital brain atlas to the T1W scan can be initiated (block 226). A user can be allowed/prompted to visually review registration results (block 227).

Is brain atlas registered to patient? (block 228). If (No) allow/prompt a user to use tools to manually correct registration of patient images to brain atlas (block 229).

If (Yes), proceed to define planning volumes (block 230).

Choose one or more volumes of interest (VOI) in images to target for treatment (block 231). The term VOI can also be referred to as a target treatment region of interest ("ROI").

Is the VOI defined in the brain atlas? (block 232). If (No) allow/prompt a user to Use VOI tools to manually define the VOI (block 234).

If (Yes), allow/prompt a user to visually review and confirm the defined VOI (block 235).

Is VOI correct? (block 236). If (No), allow/prompt a user to Use VOI tools to edit volume (block 237). If (Yes), are all VOIs defined? (block 238). If (Yes), proceed to define the regions to be avoided (NO GO)(block 240). If (No), return to block 231.

To define regions to be avoided (NO GO) (block 240), automatic or manual detection of "no-go" regions (e.g., ventricles, sulci, vessels) can be initiated (block 241).

Allow/prompt a user to visually review and confirm each NO GO region (block 243). Is the NO GO region correct? (block 244). If (No), allow/prompt a user to Use VOI tools to edit "no-go" region (block 245).

If (Yes), are all NO GO regions defined? (block 246). If (No), allow/prompt a user to use VOI tools to create a new NO GO region (block 247). If (Yes), proceed to select treatment parameters (block 250).

Allow a user to select a stereotactic frame that will be used in the clinical/surgical procedure (block 251). A list or display of options can be provided by an electronic library defining different frame options correlated to its physical parameters.

Accept user input to select at least one device that will be inserted to the target VOI for treatment during the procedure (block 253). A list or display of device options can be provided by an electronic library providing/defining different device options correlated to its physical parameters.

The system 10 can prompt/accept input from a user to select/identify a radius of treatment that will be applied during the procedure (block 255). This input can be provided by a default setting in the planning system 10 for a respective target ROI or can be provided by the physician/surgeon.

Then candidate trajectories can be determined, selected and/or confirmed (block 260). To determine and select the candidate trajectories an automatic trajectory finding method (protocol and/or algorithm) with defined rules of determining candidate trajectories can be initiated (block 261).

Each candidate trajectory can be reviewed in order of a scored ranking (block 262). During the review, the system or a user can decide whether the candidate trajectory is anatomically viable (block 263). If (No), discard or remove the candidate trajectory from being available for use (block 264).

If (Yes), determine whether the associated trajectory needs minor tweaking (block 265). If (Yes), modify the associated trajectory (block 266). If (No), accept that candidate trajectory to use for intra-operative procedure (block 267).

Determine if all candidate trajectories have been identified (block 268). If yes, the automated trajectory finding procedure can be ended. If (No), re-initiate the automated trajectory finding process (block 261).

Figure 3:
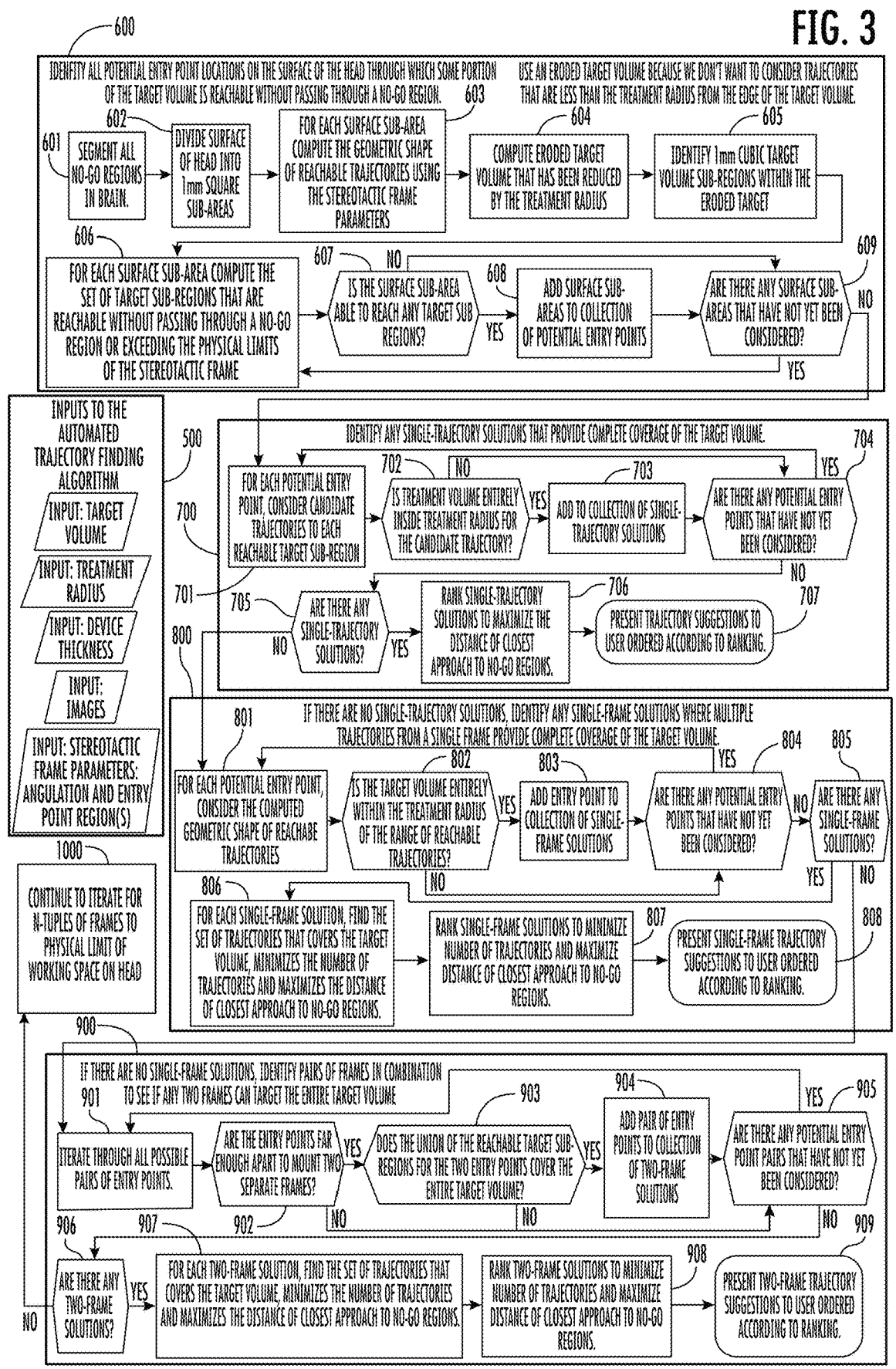
FIG. 3 is a flow chart of example actions that can be carried out to identify and rank candidate trajectories according to embodiments of the present invention.

An example of an automated trajectory finding process is shown in FIG. 3. Inputs to the automated trajectory finding system/process are provided (block 500): target VOI; treatment radius provided by an interventional device; device thickness; patient images; Stereotactic frame parameters: angulation and entry point region(s). Then, a plurality of, typically all, potential entry point locations on the outer surface of the head through which some portion of the target volume is reachable without passing through a no-go region are automatically identified (block 600). Then, any single-trajectory solutions that provide complete coverage are identified (block 700). Then, if there are no single-trajectory solutions, determine if there are any single-frame solutions where multiple trajectories from a single-frame provide complete coverage of the target volume (block 800). Then, if there are no single-frame solutions, identify pairs of frames in combination that can be concurrently coupled to the head of the patient and provide trajectories that provide complete coverage of the target volume (block 900). This process can be continued to iterate to n-multiples of frames to physical limit of working space on the head of the patient (block 1000).

For identifying the potential entry points, all no-go regions in the brain (at least those within any proximity to entry sites and target treatment volumes) can be segmented or otherwise identified (block 601). The outer surface of the head can be virtually divided into defined sub-areas, optionally with maximal outer perimeter sides in a range of 0.1 mm-2 mm, such as about 1 mm square sub-areas (block 602).

For each outer surface sub-area, the geometric shape of reachable trajectories using the stereotactic frame parameters can be determined (block 603).

An eroded target volume that has been reduced by the treatment radius can be calculated/determined (block 604). An eroded target volume can be used so that trajectories that are less than the treatment radius from the edge of the target volume are not considered. For example, an initial target volume can be identified from the digital brain atlas, which most often corresponds to an anatomical brain structure (e.g., putamen). This target volume is then "shrunk" based on its boundaries/edges relative to surrounding voxels in the acquired patient image. The reason for this is to eliminate sub-optimal trajectories in large target volumes that would require additional insertions to achieve coverage of the target volume or that are likely to provide treatment outside the target volume. When providing treatment to the specified target volume, it can be important that the candidate trajectories presented are not too close to the corresponding boundaries/edges of the target volume. Shrinking of the target volume can be accomplished using a mathematical morphology technique called "erosion", whereby voxels near the boundaries of the target volume are eroded away to provide a better representation of the volume in relation to the patient images for which the target volume is/was established for.

Target volume sub-regions within the eroded target can be identified, optionally cubic sub-volumes with sides having a length/width in a range of about 0.1 mm-2 mm, such as about 1 mm (block 605).

For each surface sub-area, a set of aligned target sub-regions that are reachable without passing through a no-go region or exceeding the physical limits of the stereotactic frame can be determined (block 606).

Determine whether the surface sub-area is able to reach any target sub regions (block 607). If yes, add the surface sub-area to a collection of potential entry points (block 608).

Determine if there are any surface sub-areas that have not yet been considered (block 609). If yes, go back to (block 606).

If no, proceed to identify any single-trajectory solutions that provide complete coverage of the target volume (block 700).

For each potential entry point associated with a respective sub-area, consider candidate trajectories to each reachable target sub-region (block 701). Is treatment volume entirely inside treatment radius for the candidate trajectory (block 702)? If yes, identify it as a single-trajectory solution and/or add this candidate trajectory to a collection of single-trajectory solutions (block 703).

If no, consider whether there are any potential entry points that have not yet been considered (block 704). If no, are there any single-trajectory solutions (block 705)? If yes, rank the single-trajectory solutions to maximize the distance of closest approach to no-go regions (block 706). Present the candidate trajectory suggestions to user ordered according to the ranking (block 707).

If there are no single-trajectory solutions, identify any single-frame solutions where multiple trajectories from a single frame provide complete coverage of the target volume (block 800).

For each potential entry point, consider the computed geometric shape of reachable trajectories (block 801). Is the target volume entirely within the treatment radius of the range of reachable trajectories (block 802)? If yes, add this surface sub-area entry point to a collection of single-frame solutions and/or identify this as a single frame solution (block 803).

Are there any potential entry points that have not yet been considered? (block 804). If no, are there any single-frame solutions? (block 805).

If yes, for each single-frame solution, find the set of trajectories that covers the target volume, minimizes the number of trajectories and maximizes the distance of closest approach to no-go regions (block 806).

Rank the single-frame solutions to minimize number of trajectories and maximize distance of closest approach to no-go regions (block 807).

Present the single-frame trajectory suggestions to user ordered according to ranking (block 808).

Figure 12:
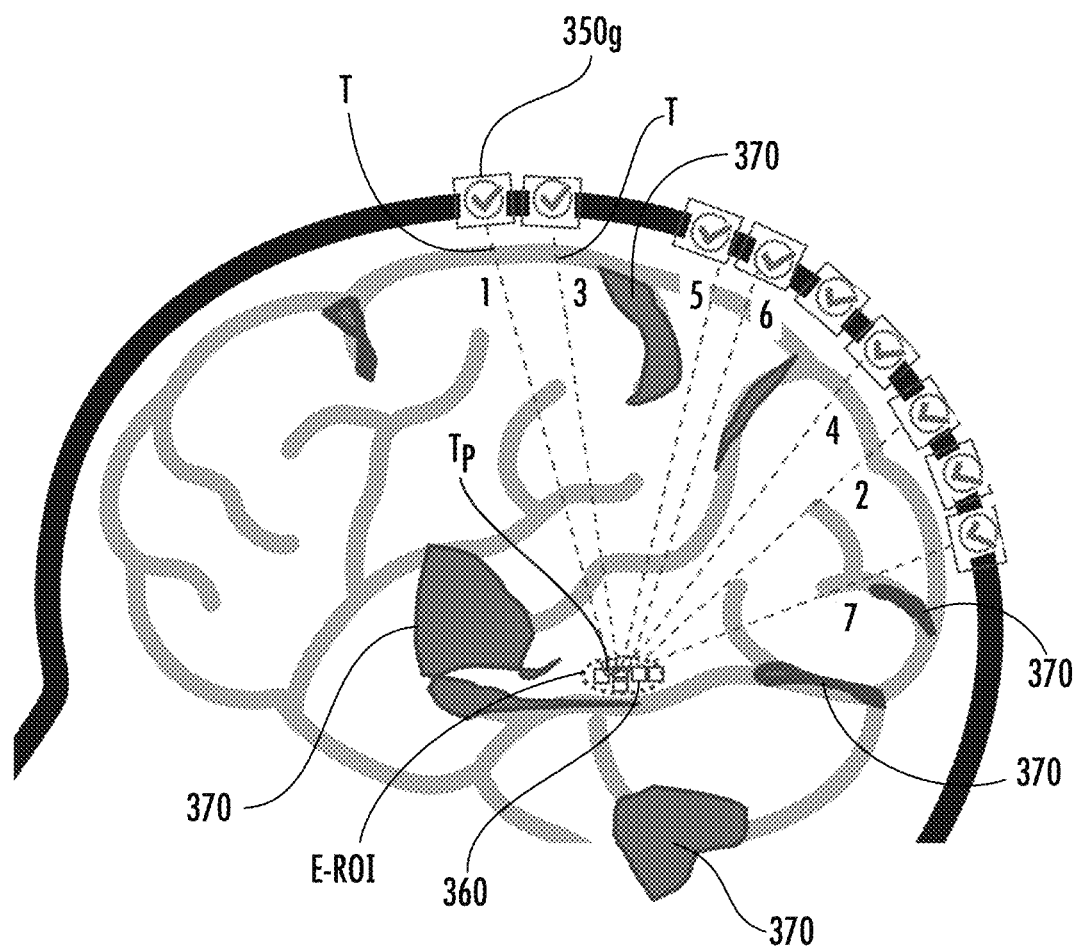
FIG. 12 illustrates the enlarged schematic illustration of FIG. 11 with rankings of preference based on defined rules according to embodiments of the present invention.
Figure 13:
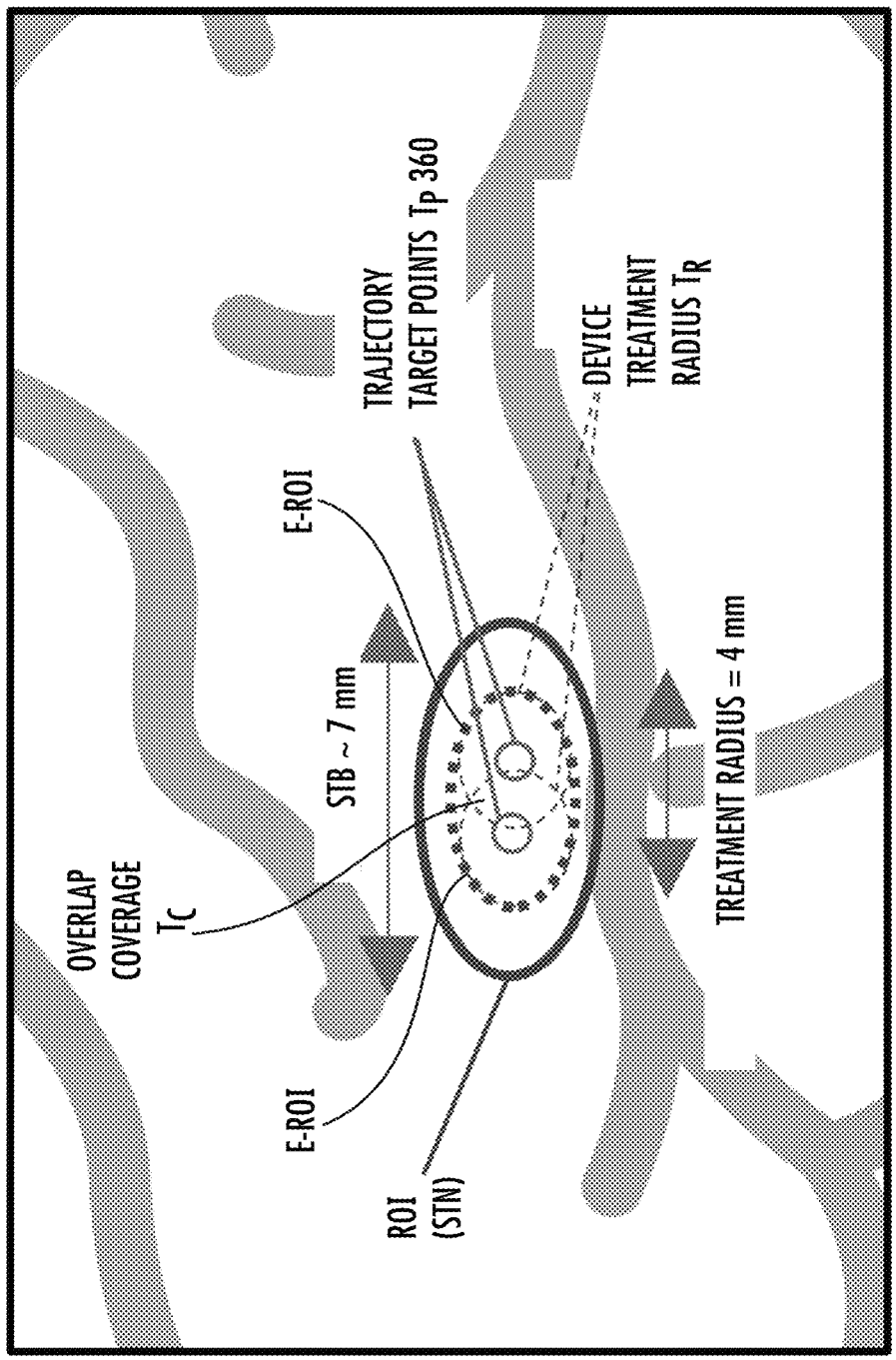
FIG. 13 is an enlarged schematic illustration of a portion of the brain shown in FIG. 12 also illustrating device treatment radii as a parameter of interest in determining acceptable/preferential candidate trajectories and/or rankings according to embodiments of the present invention.

The ranking can also consider whether complete treatment coverage is provided by a respective interventional device whether via a single trajectory end point or multiple trajectory end points Tp. The end trajectory point Tp is within the target treatment volume (ROI) and is typically associated with a respective sub-volume 360 (FIGS. 12, 13). The treatment coverage provided by an interventional device using a candidate trajectory T can also be a factor when ranking trajectory solutions. Thus, in addition to analyzing how far each proposed trajectory path is from the defined "no go" regions, the candidate trajectory protocol can also evaluate which trajectory path(s) T provide optimal coverage of the proposed treatment radius $T_R$. The radius of applied treatment $T_R$ provided by the interventional device (e.g., radius of drug infusion for infusion catheters, radius of light energy from laser applicator, radius of electrical (stimulation) signal from a DBS lead, etc.) can be used to make this determination. FIG. 13 is an enlarged schematic illustration of a portion of the brain illustrating device treatment radii $T_R$ as a parameter of interest in determining acceptable/preferential candidate trajectories and/or rankings according to embodiments of the present invention. The optimal coverage may be complete coverage of the eroded-ROI or defined treatment radius. The term "complete" with respect to "coverage" means that the interventional device is able to treat within +/−10% of the entire E-ROI or defined treatment radius using one or more trajectory paths T.

If there are no single-frame solutions, identify pairs of frames in combination to see if any two frames can cover the entire target volume (block 900).

Iterate through all possible pairs of entry points defined by each frame (block 901). Are the entry points far enough apart to concurrently mount two separate frames to the head of the patient? (block 902). If yes, does the union of the reachable target sub-regions for the two entry points cover the entire target treatment volume? (block 903).

If yes, add the pair of entry points to collection of two-frame solutions and/or otherwise identify the pair (block 904).

Are there any potential entry point pairs that have not yet been considered? (block 905). If not, are there any two-frame solutions? (block 906). If not, continue to iterate for n-multiples of frames to physical limit of working space on head (block 1000).

If yes, for each two-frame solution, find the set of trajectories that covers the target volume, minimizes the number of trajectories and maximizes the distance of closest approach to no-go regions (block 907).

Rank two-frame solutions to minimize number of trajectories and maximize distance of closest approach to no-go regions (block 908).

The two-frame candidate trajectory suggestions can be presented to the user, ordered according to ranking (block 909).

Figure 4A:
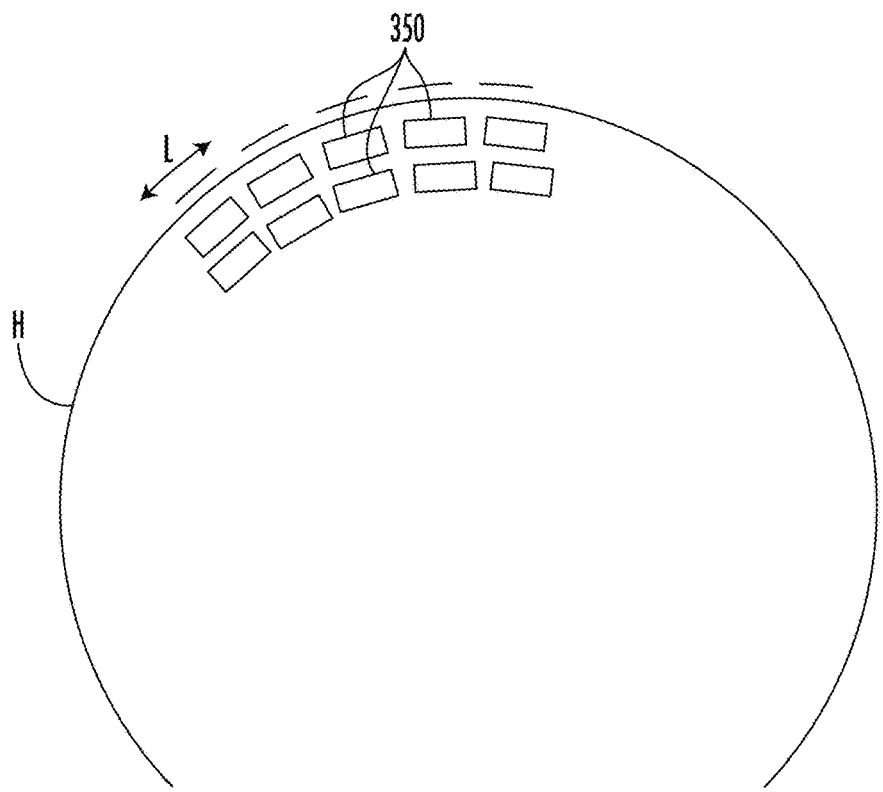
FIG. 4A is a schematic illustration of a patient head with an outer surface virtually divided into sub-areas according to embodiments of the present invention.

FIG. 4A schematically illustrates virtual (outer) surface sub-areas 350 of a head/skull that can be used to identify potential entry locations. These sub-areas 350 can have sides that are shared or may overlap, share a side boundary or be closely spaced apart, such as neighbors residing within by about 0.01 mm of each other. These sub-areas 350 can have a common geometrical shape and size. These sub-areas 350 can have a different geometrical shape and size. These sub-areas 350 may have some that are concave to conform to the shape of the head/skull of a patient. The sub-areas 350 can have an outer perimeter side with a maximal length or width ("L") that is in a range of about 0.1 mm to about 2 mm, such as about 1 mm. The sub-areas 350 can have a square shape.

Figure 4B:
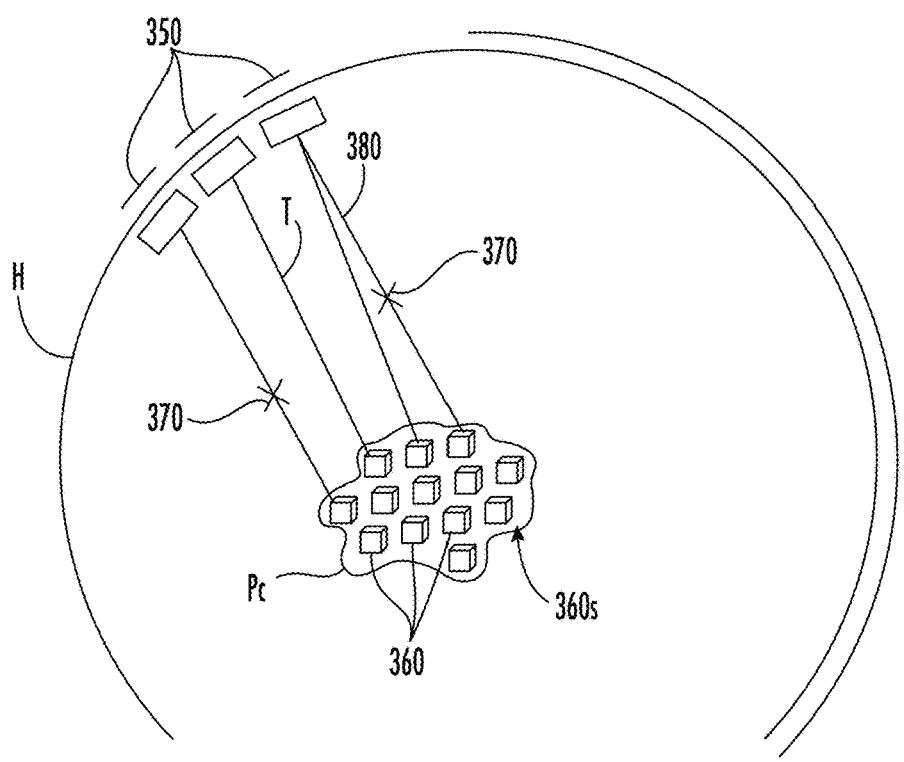
FIG. 4B is a schematic illustration of the patient head shown in FIG. 4A with internal regions to target divided into sub-volumes, optionally also or alternatively using rays from ray casting, for identifying appropriate candidate trajectories based on defined rules according to embodiments of the present invention.

FIG. 4B schematically illustrates a target region of interest (ROI) that the user in the brain inside the head H of a patient. The ROI can optionally be defined by a sub-volume 360 and/or divided into virtual (target) sub-volumes 360. Adjacent (target) sub-volumes 360 can share perimeter side boundaries or be closely spaced apart within a defined range such as 0.1 mm. Candidate trajectories T can be considered from each sub-area 350 to any one or more sub-volume 360, typically to a single one sub-volume 360. The sub-volumes 360 are created by dividing the target region of interest (e.g., putamen) into a set of digital sub-volumes that make up that target region of interest. Respective sets 360s of target sub-volumes 360 that align with trajectories that extend from a respective surface sub-area 350 and that do not extend through a NO GO region 370 can be used to identify a respective viable candidate trajectory T.

Optionally, virtual ray casting can be used to cast rays 380 from a sub-area 350 to any sub-area 360, excluding those ray casts which extend through a NO GO region 370.

These sub-volumes 360 can be cubic sub-volumes having maximal lengths/widths (L) of an outer perimeter side in a range of 0.1 mm to 2 mm, optionally about 1 mm in some embodiments. The sub-volumes 360 can have a maximal length/width L that is the same as that of the sub-areas 350.

The target treatment region can be represented by a point cloud or point clouds Pc, such as a spherical point cloud in some embodiments.

Embodiments of the present invention may take the form of an entirely software embodiment or an embodiment combining software and hardware aspects, all generally referred to herein as a "circuit" or "module." Furthermore, the present invention may take the form of a computer program product on a (non-transient) computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of data processing systems, method steps or actions, modules or circuits (or portions thereof) discussed herein may be written in a high-level programming language, such as Python, Java, AJAX (Asynchronous JavaScript), C, and/or C++, for development convenience. In addition, computer program code for carrying out operations of exemplary embodiments may also be written in other programming languages, such as, but not limited to, interpreted languages. Some modules or routines may be written in assembly language or even micro-code to enhance performance and/or memory usage. However, embodiments are not limited to a particular programming language. As noted above, the functionality of any or all of the program modules may also be implemented using discrete hardware components, one or more application specific integrated circuits (ASICs), or a programmed digital signal processor or microcontroller. The program code may execute entirely on one (e.g., a workstation) computer, partly on one computer, as a stand-alone software package, partly on the workstation's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

The present invention is described in part with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality. The AC, PC and MSP locations of images of a brain of respective patients can be identified in any suitable manner. For example, AC, PC and MSP locations can be identified through the digital brain atlas after it is registered with patient images.

Although not shown, in some embodiments, one or more of the surgical tools can be configured with one or more lumens and exit ports that deliver desired therapies, optionally cellular, biological, and/or drug therapeutics to the target area, such as the brain. The tools may also incorporate transseptal needles, biopsy and/or injection needles as well as thermal therapy devices. The lumens, where used, may receive extendable needles that may exit the probe from the distal end or from the sides, proximal, distal, or even, through the active element (e.g., thermal element such as electrodes) to precisely deliver cellular/biological therapeutics to the desired anatomy target. This delivery configuration may be a potential way to treat patients, where the cellular/biological therapeutics can be delivered into the desired anatomy to modify their cellular function. The cells (e.g., stem cells) may improve function. The thermal hyperthermia devices may be used to facilitate cell lysing to stimulate the immune system. MRI can typically be effectively used to monitor the efficacy and/or delivery of the therapy.

Figure 6:
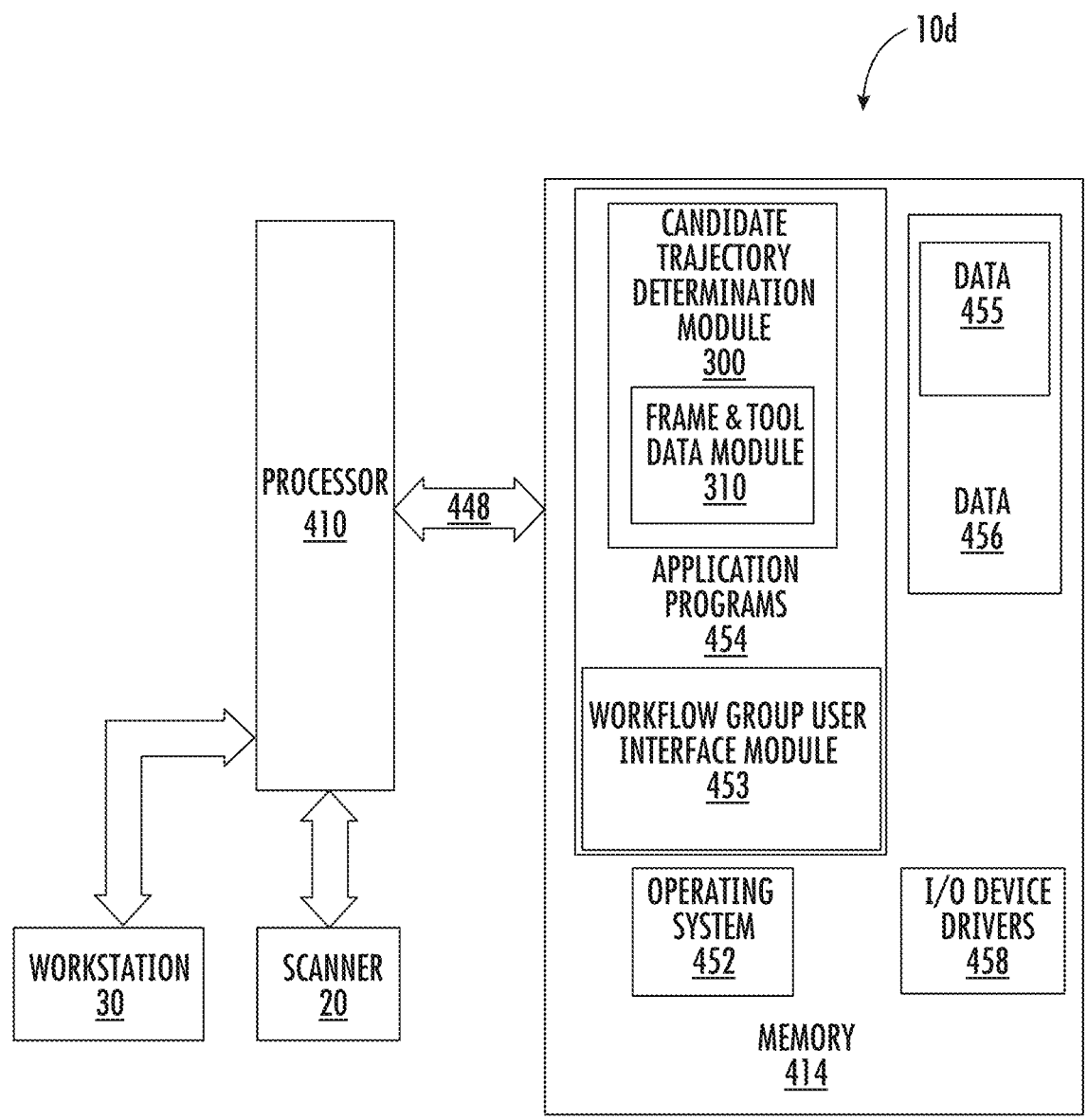
FIG. 6 is a schematic illustration of an example data processing system according to some embodiments of the present invention.

FIG. 6 is a schematic illustration of a data processing system 10d that can be used with the surgical planning system 10. The data processing system may be incorporated in one or more digital signal processors in any suitable device or devices. As shown in FIG. 6, the processor 410 can communicate with or be onboard the workstation 30 and/or can communicate with a scanner 20 and with memory 414 via an address/data bus 448. The processor 410 can be any commercially available or custom microprocessor. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

As shown in FIG. 6 the memory 414 may include several categories of software and data used in the data processing system: the operating system 452; the application programs 454; the input/output (I/O) device drivers 458; and data 456. The data 456 can also include predefined characteristics of different surgical tools and frames and patient image data 455. FIG. 6 also illustrates the application programs 454 can include a Candidate Trajectory Determination Module 300, and a Frame and Tool Data Module 310, and a workflow group User Interface Module 453 (that facilitates user actions and provides user review of candidate trajectories for example).

As will be appreciated by those of skill in the art, the operating systems 452 may be any operating system suitable for use with a data processing system, such as OS/2, AIX, DOS, OS/390 or System 390 from International Business Machines Corporation, Armonk, NY, Window versions from Microsoft Corporation, Redmond, WA, Unix or Linux or FreeBSD, Palm OS from Palm, Inc., Mac OS from Apple Computer, LabView, or proprietary operating systems. The I/O device drivers 458 typically include software routines accessed through the operating system 452 by the application programs 454 to communicate with devices such as I/O data port(s), data storage 456 and certain memory 414 components. The application programs 454 are illustrative of the programs that implement the various features of the data processing system and can include at least one application, which supports operations according to embodiments of the present invention. Finally, the data 456 represents the static and dynamic data used by the application programs 454, the operating system 452, the I/O device drivers 458, and other software programs that may reside in the memory 414.

While the present invention is illustrated, for example, with reference to the Modules 300, 310 being application programs in FIG. 6, as will be appreciated by those of skill in the art, other configurations may also be utilized while still benefiting from the teachings of the present invention. For example, the Modules 300, 310 may also be incorporated into the operating system 452, the I/O device drivers 458 or other such logical division of the data processing system. Thus, the present invention should not be construed as limited to the configuration of FIG. 6 which is intended to encompass any configuration capable of carrying out the operations described herein. Further, one or more of modules, i.e., Modules 300, 310 can communicate with or be incorporated totally or partially in other components, such as a workstation, a scanner such as an MRI scanner, an interface device. Typically, the workstation 30 will include the modules 300, 310 and the scanner can include a module that communicates with the workstation 30 and can push image data thereto.

The I/O data port can be used to transfer information between the data processing system 10d, the computer system 10c, the circuit 30c or workstation 30, the scanner 20, and another computer system or a network (e.g., the Internet) or to other devices controlled by or in communication with the processor. These components may be conventional components such as those used in many conventional data processing systems, which may be configured in accordance with the present invention to operate as described herein.

Embodiments of the invention will be described further below with respect to the non-limiting Examples.

EXAMPLES

FIGS. 7A-7C, 8A, 8B and 9-11 illustrate an automatic trajectory plan for a unilateral procedure for placing a deep brain stimulation electrode in a brain of a patient targeting the sub-thalamic nucleus (STN).

Figure 7A:
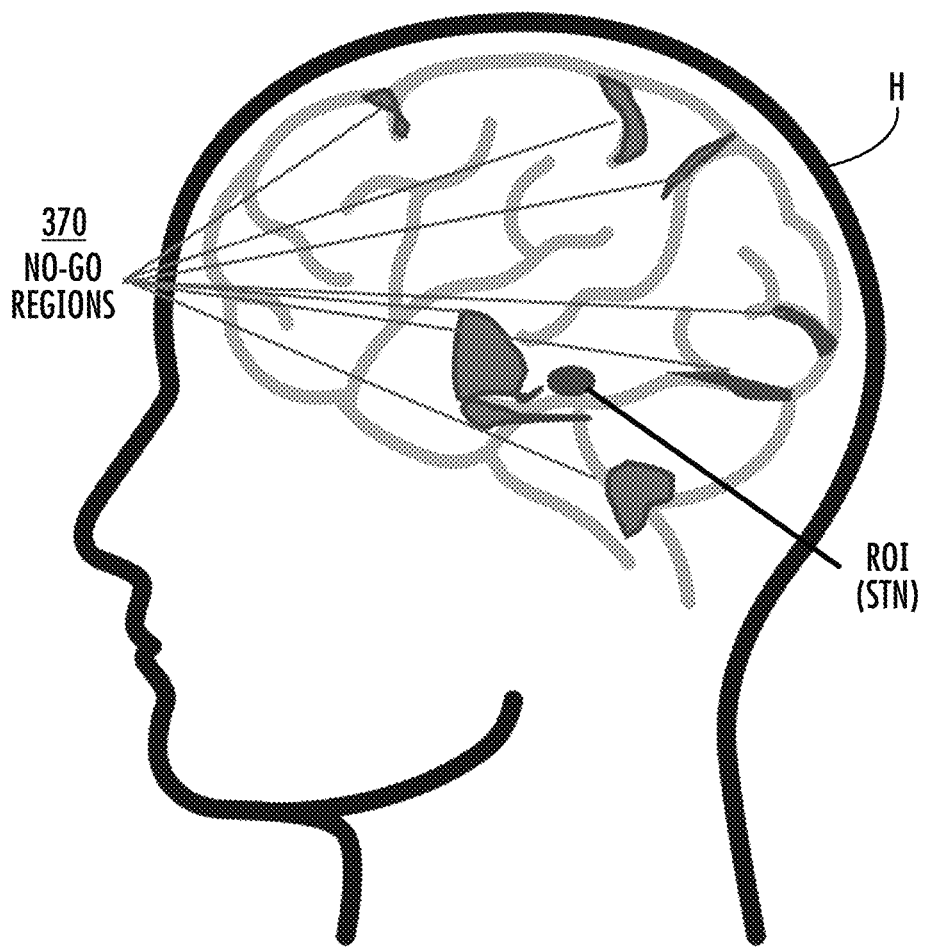
FIG. 7A is a schematic illustration of a brain illustrating defined no-go regions for a target region of interest corresponding to a sub-thalamic nucleus (STN) according to some embodiments of the present invention.

FIG. 7A illustrates automatic identification of structures in the brain (segmentation to define no-go regions) to be avoided during trajectory planning targeting the STN, such as blood vessels, ventricles and sulci of the cortex which are identified as "no-go" regions 370.

Figure 7B:
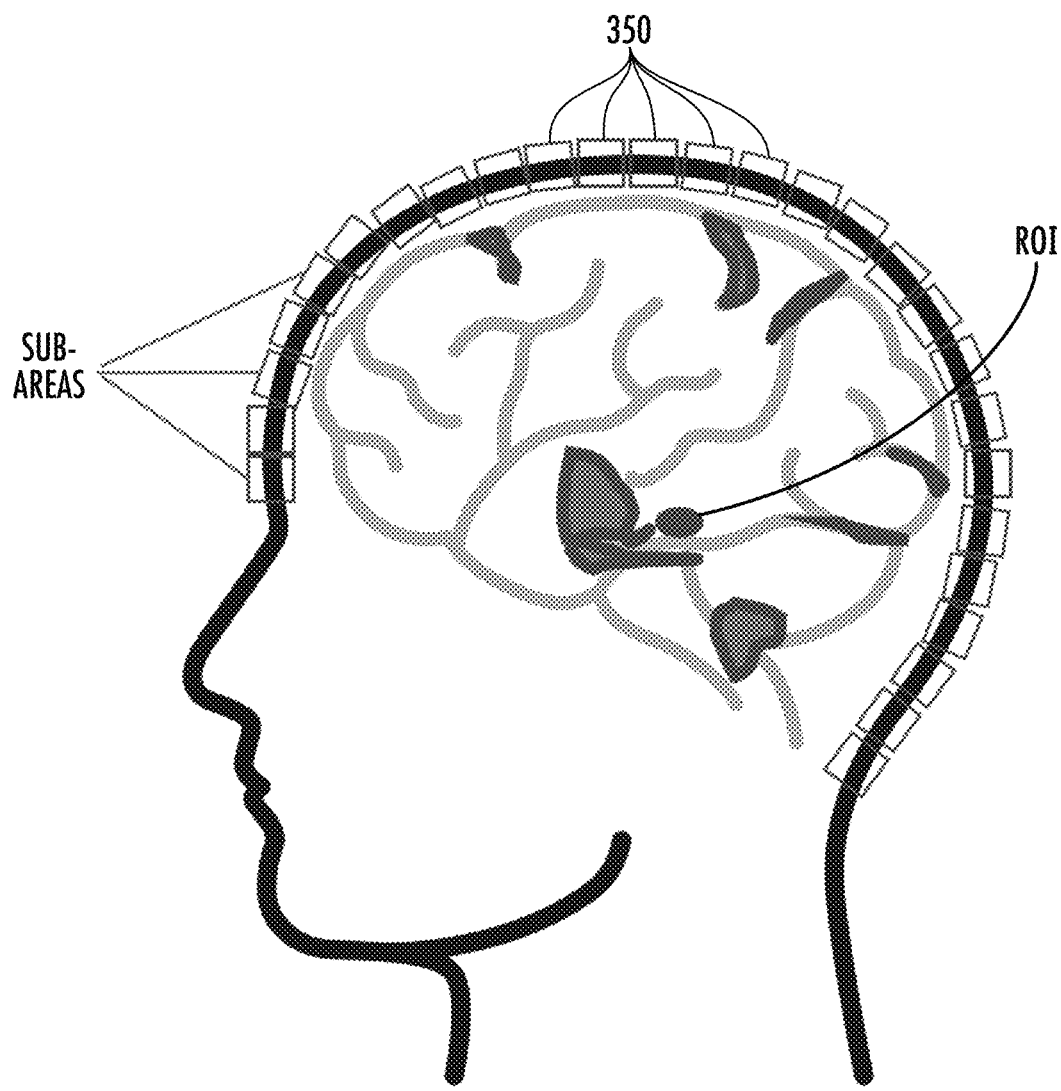
FIG. 7B illustrates the schematic illustration of FIG. 7A with the head having sub-areas defined for locating candidate entry point locations on the patient according to embodiments of the present invention.

FIG. 7B illustrates virtually dividing the head surface into sub-areas 350, optionally as square or rectangular sub-areas as shown. The entire three-dimensional head surface area can be divided into the sub-areas 350 from the front of the head (above and/or adjacent the orbital sockets) to lower back of the head adjacent the upper portion of the neck. The sub-areas can be used to automatically identify candidate entry point locations on the patient.

Figure 7C:
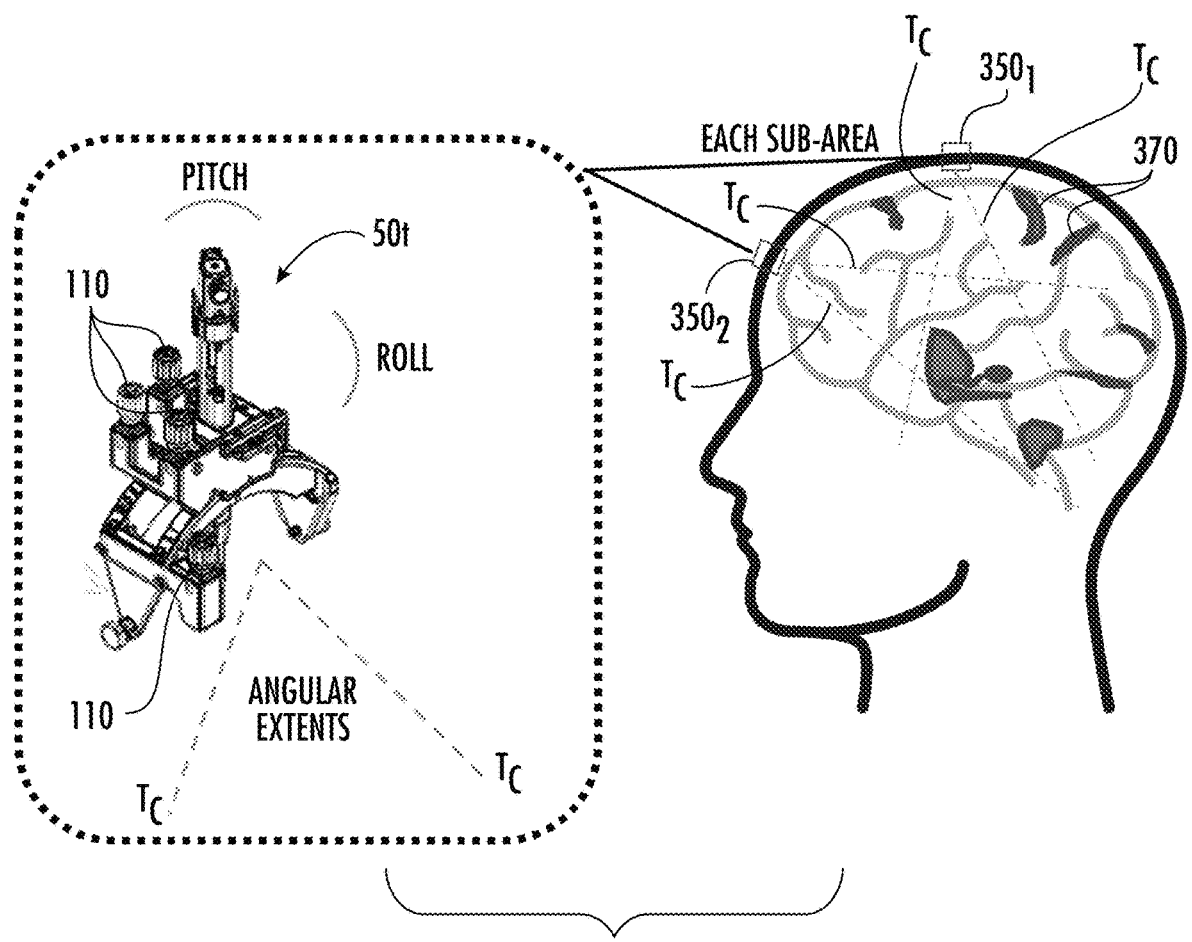
FIG. 7C illustrates the schematic illustration of FIG. 7B with an example sub-area and physical constraints of trajectories therefrom defined by stereotactic frame/trajectory guide angular extent limitations according to embodiments of the present invention.

FIG. 7C illustrates that for each sub-rea 350, a geometric shape of reachable trajectories are computed using stereotactic frame parameters. For example, the trajectory frame/guide 50t can have two degrees of angular freedom, such as pitch (+/− 33 degrees) and roll (+/− 26 degrees). The angular extents allowed by the trajectory frame/guide 50t can be determined based on the maximum degrees of freedom in each direction. Any reachable trajectories within a given surface sub-area (a sub-area of 1 mm$^2$, for example) need to fall within a virtual cone Tc representing the angular extents of the frame/guide 50t. Other trajectory guides/frames may have other angular extents and configurations.

Figure 8A:
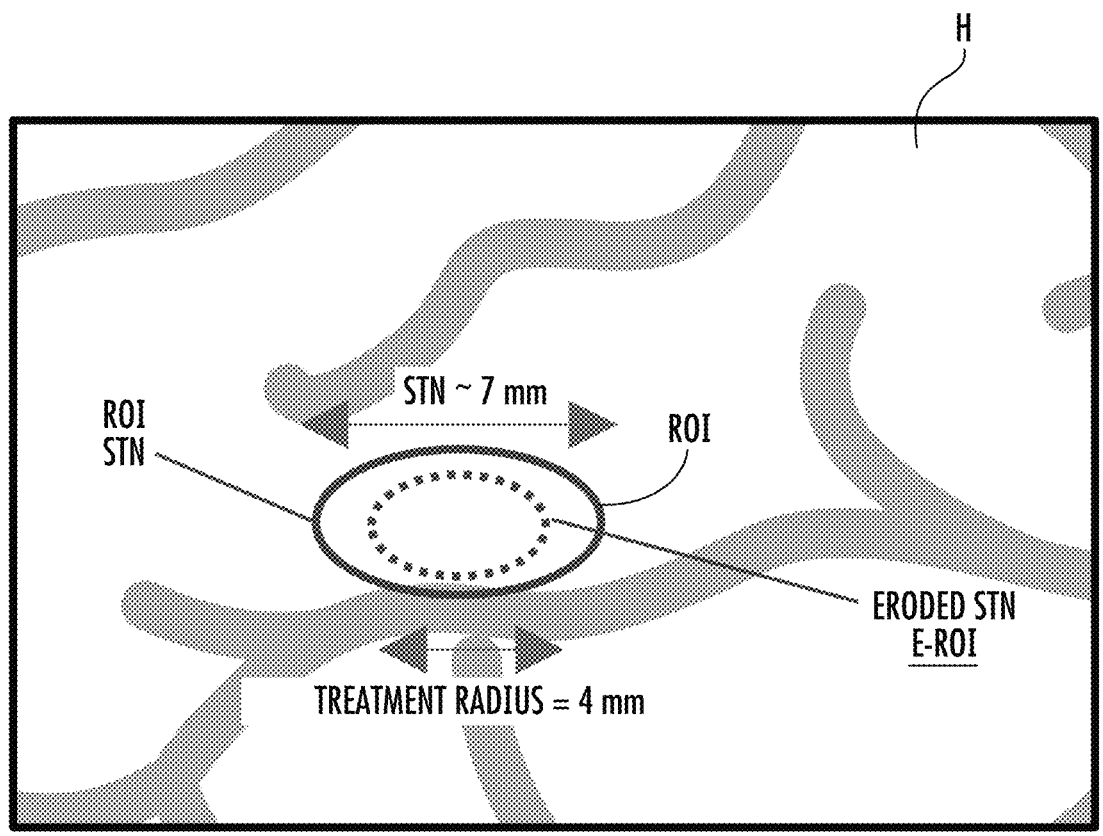
FIG. 8A is an enlarged schematic illustration of a portion of the brain shown in FIGS. 7A-7C, illustrating an eroded target volume according to embodiments of the present invention.

FIG. 8A illustrates an eroded target volume (E-ROI) of the ROI (STN) reduced by a treatment radius. In the example shown, the STN has a radius of about 7 mm and the eroded target volume (E-ROI) is about 4 mm. That is, the size of the STN is about 7 mm. The eroded volume is smaller than the actual size of the ROI (STN). The eroded volume/structure represents the area within the STN that is typically treated (dorsal lateral end) using deep brain stimulation. This smaller area is typically about 4 mm. The eroded ROI volume (E-ROI) can be used because those trajectories are less than the proposed treatment radius from an edge of the STN that should not be considered as suitable paths into the brain. This provides a safe sub-region for targeting within the overall ROI, which also adequately covers the proposed radius of treatment.

Figure 8B:
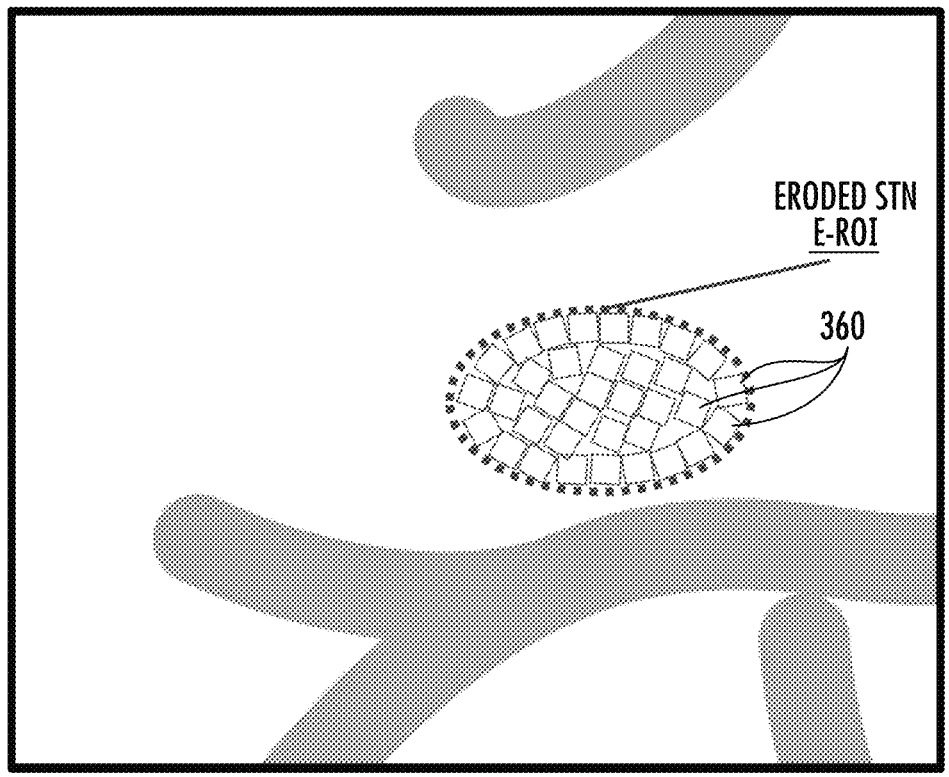
FIG. 8B is a schematic illustration of FIG. 8A illustrating sub-regions defined in the eroded target volume according to embodiments of the present invention.

FIG. 8B is a schematic illustration of sub-regions 360 within the eroded target volume (E-ROI). The eroded target volume (eroded STN) can be sub-divided into sub-regions, such as sub-volumes of about 1 mm$^3$.

Figure 9:
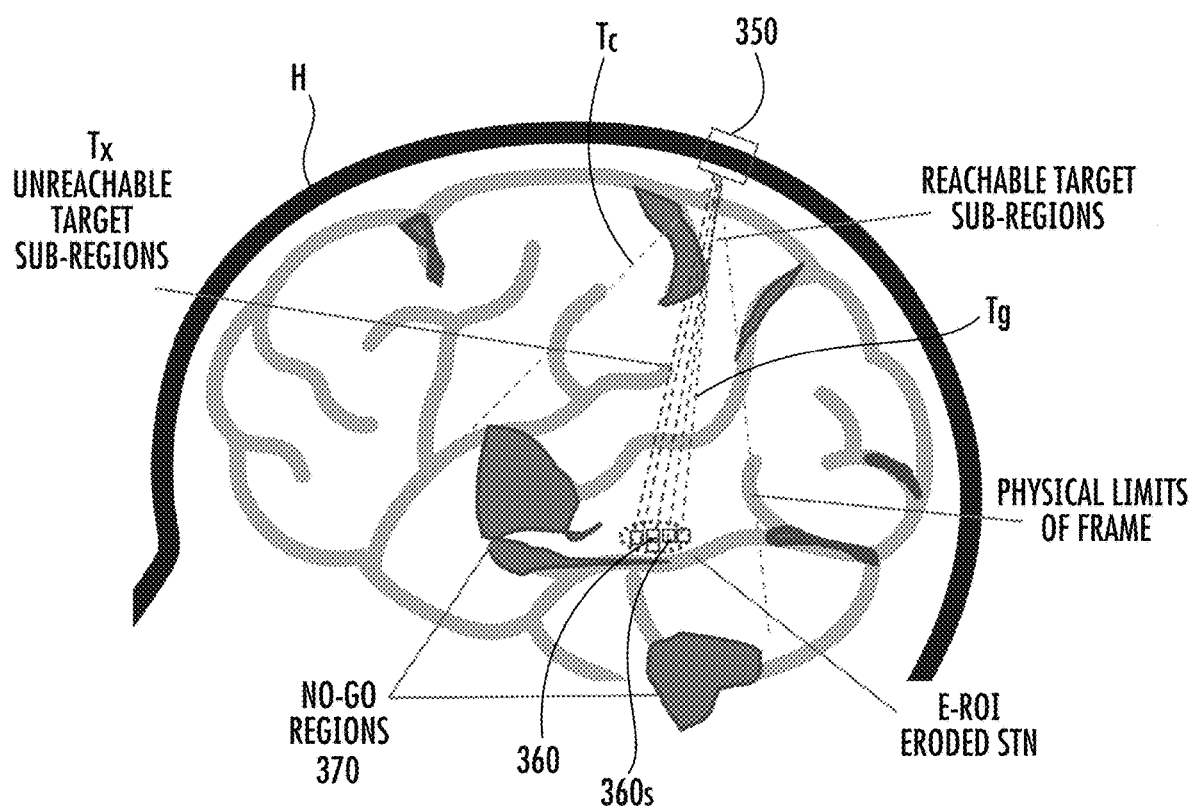
FIG. 9 is an enlarged schematic illustration of a portion of the brain shown in FIG. 7A with an example sub-area and sub-volumes with trajectories defining reachable and unreachable trajectory paths to the region of interest according to embodiments of the present invention.

FIG. 9 illustrates that for each sub-area 350, reachable target sub-regions 360 trajectories Tg are identified and unreachable target-sub-regions 360 trajectories Tx (those that approach or go through n-go regions) are identified, all within the cone Tc defining the physical limits of the trajectory guide 50t. There can be more than one reachable target sub-region trajectory for each sub-area 350. For example, for each (e.g., 1 mm²) sub-area 350 on the surface of the head, a set 360s of target sub-regions 360 (e.g., 1 mm³) that are reachable are identified. A target sub-region 360 is considered reachable if it lies within the cone Tc representing the physical limits of the trajectory guide 50t and does not intersect a no-go region 370. FIG. 9 shows an example of reachable target sub-regions 360 from a single surface sub-area 350 (which can have a size of about 1 mm²).

Figure 10:
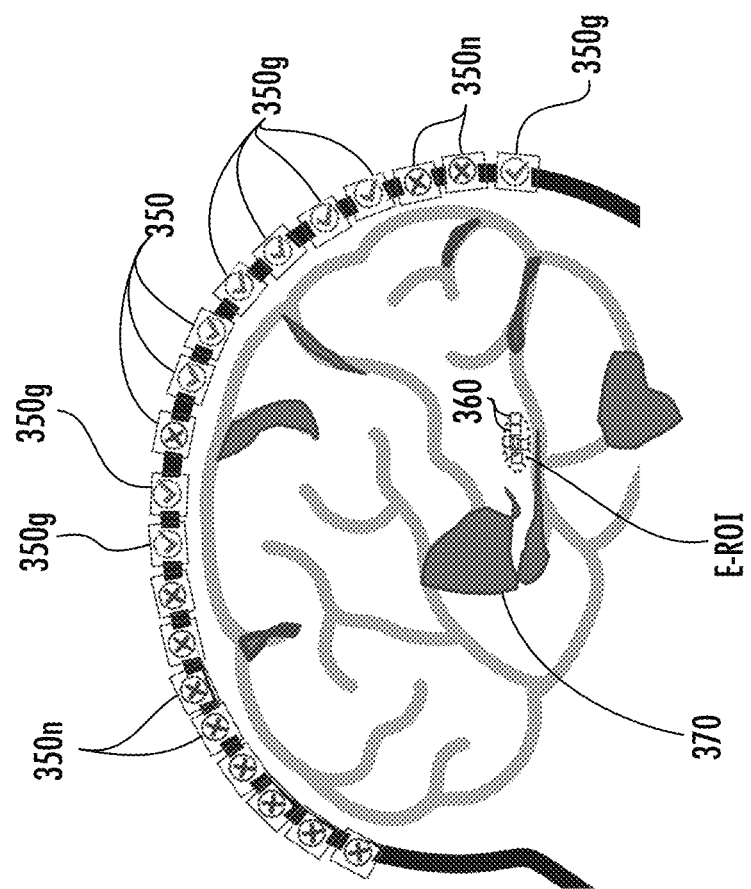
FIG. 10 illustrates the enlarged schematic illustration of the portion of the brain shown in FIG. 9 with different sub-areas identified as viable or non-viable entry point candidates according to embodiments of the present invention.

FIG. 10 illustrates that entry point candidates can be identified using the sub-areas 350. For each sub-area 350 that defines at least one trajectory T that can reach a target sub-volume 360 of an eroded STN, that sub-area 350g shown as a sub-rea with a "check mark" can be included in a collection or set of potentially viable entry point options for trajectory paths T into the brain and to the target ROI. Non-viable sub-areas 350n identified with an "X" in FIG. 10, can be discarded or otherwise not further considered. The viable sub-surface areas 350g identifying viable entry point candidates can be collected.

Figure 11:
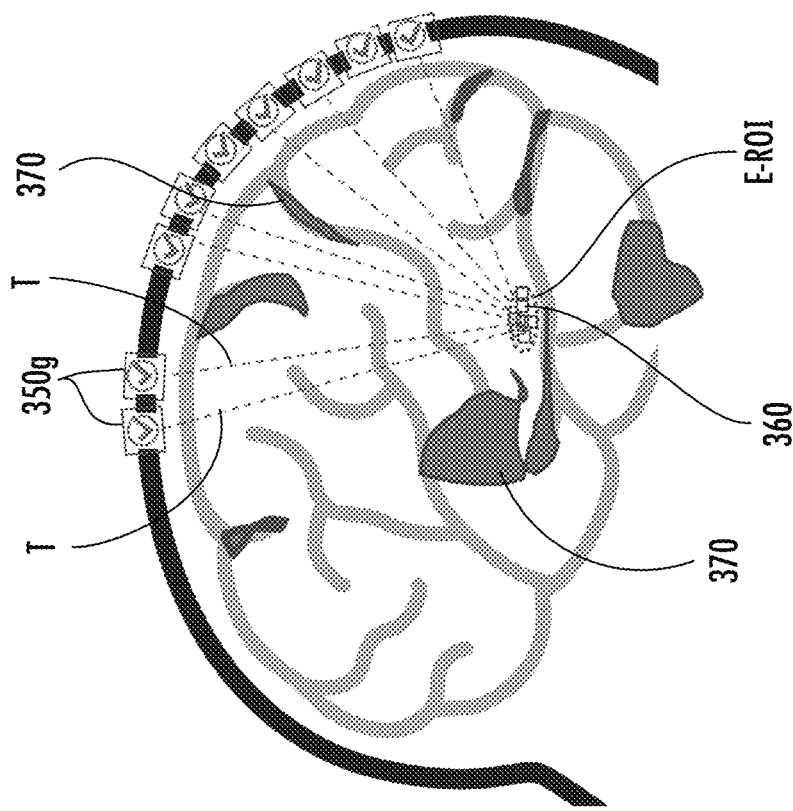
FIG. 11 illustrates the enlarged schematic illustration of FIG. 10 with different sub-areas to different sub-volumes of the region of interest and corresponding trajectories according to embodiments of the present invention.

FIG. 11 shows that any single-trajectory T from a respective viable sub-area 350g that can provide coverage of the target ROI, e.g., E-ROI, are identified. That is, it is determined whether from each surface sub-area 350 a single trajectory T can be used to achieve complete coverage of the eroded STN structure, E-ROI. If multiple trajectories are required in order to achieve complete treatment coverage of the E-ROI (eroded STN), based on the trajectory guide/ frame's 50t angular extent limitations and/or "no-go" regions 370 and/or interventional device treatment radius, iterations of multiple trajectory guide/frames 50t can be performed.

FIG. 12 illustrates that single-trajectory solutions can be ranked to allow the trajectory T that is farther away from any "no-go" region 370 for preferentially selecting or proposing that respective trajectory for use during a medical procedure, e.g., implanting the DBS lead. The single-trajectory solutions can be ranged based on how close they are to "no-go" regions 370. Those furthest away from any "no-go" regions can be given higher ranking order than those closer to one or more "no-go" regions 370. Typically, a safer trajectory path will be the one furthest away from any "no-go" region 370. The rankings are shown as 1-7 in the example illustration, with number one (1) being the furthest from a non-go location, then number two (2) being the next furthest from one or more of the identified no-go regions.

FIG. 13 is an enlarged schematic illustration of a portion of the brain illustrating a respective device treatment radii $T_R$ as a parameter of interest in determining acceptable/ preferential candidate trajectories T and/or rankings according to embodiments of the present invention. As shown, there are two trajectory target points Tp, each having an associated treatment radius $T_R$ and the different treatment radii can be the same (as the same interventional device is used at different trajectory paths T to a corresponding trajectory point Tp and/or sub-volume 360) and the different treatment radii can partially overlap while fitting within the eroded-ROI (E-ROI)/treatment radius. The device treatment radii $T_R$ can be defined for different interventional procedures, such as in a look-up table or other database, and/or provided as an input parameter for a respective interventional procedure.

In the drawings and specification, there have been disclosed embodiments of the invention and, although specific terms are employed, they are used in a generic and descriptive sense only and not for purposes of limitation, the scope of the invention being set forth in the following claims. Thus, the foregoing is illustrative of the present invention and is not to be construed as limiting thereof. More particularly, the workflow steps may be carried out in a different manner, in a different order and/or with other workflow steps or may omit some or replace some workflow steps with other steps. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A surgical planning system, comprising:
    a workstation comprising a display; and
    a computer system in communication with or at least partially onboard the workstation, wherein the computer system is configured to:
        provide at least one image of a brain of a patient;
        register a digital brain atlas to the at least one image;
        accept user input to confirm and/or identify at least one target treatment region in the brain of the patient;
        determine regions in the brain that are to be avoided;
        identify one candidate trajectory or a plurality of different candidate trajectories for providing a respective trajectory path from a location external to the patient to the at least one target treatment region as a surgical treatment path;
        accept user input to either input stereotactic frame parameters of a stereotactic frame or select a stereotactic frame from defined stereotactic frames that will be used during a surgical procedure to identify angulation and entry point regions thereof;
        define a desired treatment radius of the at least one target treatment region; and
        identify and/or select a surgical device that will be used to carry out a desired surgical treatment,
    wherein, in response to the identification or selection, the computer system is configured to provide corresponding physical parameters including thickness and a length of the identified and/or selected surgical device, and wherein the identifying the one or the plurality of candidate trajectories uses the provided physical parameters as computational inputs.

2. The system of claim 1, wherein the identified one candidate trajectory or the identified plurality of candidate trajectories is/are identified by:

dividing a surface of a head of the patient into defined sub-areas that correspond to potential entry sites into the brain;

dividing one or more target volumes associated with the at least one target treatment region within the brain into sub-volumes; and identifying, for at least some of the sub-areas, a respective trajectory to one or more of the sub-volumes that does not pass through any of the determined regions to be avoided to define a respective candidate trajectory.

3. The system of claim 1, wherein the identified one candidate trajectory or the identified plurality of candidate trajectories is/are identified by:

dividing a surface of a head of the patient into defined sub-areas that correspond to potential entry sites into the brain; and for at least some of the defined sub-areas, ray casting to identify virtual rays that do not pass through any of the determined regions to be avoided and that extend to at least a portion of the at least one target treatment region whereby, if so, a respective surface sub-area and corresponding ray path define a respective candidate trajectory.

4. The system of claim 1, wherein the computer system is configured to provide electronically selectable surgical devices comprising at least one of:

an intrabrain fluid delivery device;

an intrabrain fluid/tissue withdrawal device;

a thermal therapy device; and an implantable electrode(s).

5. The system of claim 1, wherein the computer system is further configured to accept user input to:

edit a volume associated with the at least one target treatment region; and edit determined regions that are to be avoided for the trajectory path.

6. The system of claim 1, wherein the computer system is configured to identify the plurality of different candidate trajectories and provide the plurality of different candidate trajectories in a ranked order based on defined rules and/or parameters.

7. The system of claim 1, wherein the computer system is configured to identify the plurality of different candidate trajectories and provide the plurality of different candidate trajectories in a ranked order.

8. The system of claim 1, wherein the surgical planning system electronically controls a motor drive system to turn actuators coupled to a trajectory guide that adjust a trajectory of the trajectory guide to provide a selected candidate trajectory from the one identified candidate trajectory or from the plurality of candidate trajectories for a surgical procedure.

9. The system of claim 1, in combination with a CT or MRI scanner, wherein the workstation is in communication with the CT or MRI scanner, and wherein the workstation comprises a DICOM interface that receives images from the CT or MRI scanner to provide the at least one image for the surgical planning system.

10. A surgical planning system, comprising:

a workstation comprising a display; and a computer system in communication with or at least partially onboard the workstation, wherein the computer system is configured to:

provide at least one image of a brain of a patient;

register a digital brain atlas to the at least one image;

accept user input to confirm and/or identify at least one target treatment region in the brain of the patient;

determine regions in the brain that are to be avoided;

identify one candidate trajectory or a plurality of different candidate trajectories for providing a respective trajectory path from a location external to the patient to the at least one target treatment region as a surgical treatment path, wherein the identified one candidate trajectory or the identified plurality of candidate trajectories is/are identified by:

dividing a surface of a head of the patient into defined sub-areas that correspond to potential entry sites into the brain; and for at least some of the defined sub-areas, ray casting to identify virtual rays that do not pass through any of the determined regions to be avoided and that extend to at least a portion of the at least one target treatment region whereby, if so, a respective surface sub-area and corresponding ray path define a respective candidate trajectory, wherein the computer system is further configured to divide the at least one target treatment region within the brain into sub-volumes before the ray casting, wherein the ray casting is carried out to identify whether a virtual ray extending from a respective sub-area to one or more of the sub-volumes does not pass through any of the determined regions to be avoided.

11. A surgical planning system, comprising:

a workstation comprising a display; and a computer system in communication with or at least partially onboard the workstation, wherein the computer system is configured to:

provide at least one image of a brain of a patient;

register a digital brain atlas to the at least one image;

accept user input to confirm and/or identify at least one target treatment region in the brain of the patient;

determine regions in the brain that are to be avoided; and identify one candidate trajectory or a plurality of different candidate trajectories for providing a respective trajectory path from a location external to the patient to the at least one target treatment region as a surgical treatment path;

wherein the computer system is configured to identify an eroded target volume of the at least one target treatment region that is reduced in volume from an original volume of the at least one target treatment region by a defined treatment radius, and wherein the identified candidate trajectory or the identified plurality of candidate trajectories extend from a defined sub-area associated with a candidate entry site into the brain to a sub-volume within the eroded target volume.

12. A surgical planning system, comprising:

a workstation comprising a display; and a computer system in communication with or at least partially onboard the workstation, wherein the computer system is configured to:

provide at least one image of a brain of a patient;

register a digital brain atlas to the at least one image;

accept user input to confirm and/or identify at least one target treatment region in the brain of the patient;

determine regions in the brain that are to be avoided; and identify one candidate trajectory or a plurality of different candidate trajectories for providing a respective trajectory path from a location external to the patient to the at least one target treatment region as a surgical treatment path;

wherein the identified one candidate trajectory or the identified plurality of candidate trajectories is/are identified by:
dividing a surface of a head of the patient into defined sub-areas that correspond to potential entry sites into the brain;
dividing one or more target volumes associated with the at least one target treatment region within the brain into sub-volumes; and
identifying, for at least some of the sub-areas, a respective trajectory to one or more of the sub-volumes that does not pass through any of the determined regions to be avoided to define a respective candidate trajectory,
wherein the defined sub-areas have a defined geometric shape, with a maximal length of an outer perimeter side thereof in a range of 0.1 mm-2 mm.

13. The system of claim 12, wherein the defined sub-areas have a square geometric shape.

14. A surgical planning system, comprising:
a workstation comprising a display; and
a computer system in communication with or at least partially onboard the workstation, wherein the computer system is configured to:
provide at least one image of a brain of a patient;
register a digital brain atlas to the at least one image;
accept user input to confirm and/or identify at least one target treatment region in the brain of the patient;
determine regions in the brain that are to be avoided; and
identify one candidate trajectory or a plurality of different candidate trajectories for providing a respective trajectory path from a location external to the patient to the at least one target treatment region as a surgical treatment path;
wherein the identified one candidate trajectory or the identified plurality of candidate trajectories is/are identified by:
dividing a surface of a head of the patient into defined sub-areas that correspond to potential entry sites into the brain;
dividing one or more target volumes associated with the at least one target treatment region within the brain into sub-volumes; and
identifying, for at least some of the sub-areas, a respective trajectory to one or more of the sub-volumes that does not pass through any of the determined regions to be avoided to define a respective candidate trajectory,
wherein the sub-volumes are cubic sub-volumes with a maximal length of an outer perimeter side thereof in a range of about 0.1 mm-2 mm.

15. A surgical planning system, comprising:
a workstation comprising a display; and
a computer system in communication with or at least partially onboard the workstation, wherein the computer system is configured to:
provide at least one image of a brain of a patient;
register a digital brain atlas to the at least one image;
accept user input to confirm and/or identify at least one target treatment region in the brain of the patient;
determine regions in the brain that are to be avoided; and
identify one candidate trajectory or a plurality of different candidate trajectories for providing a respective trajectory path from a location external to the patient to the at least one target treatment region as a surgical treatment path;
wherein the computer system provides user-selectable input parameters of:
a plurality of different stereotactic frames, each having an associated electronically defined physical limit of operation for providing adjustable/selectable trajectory paths; and
a plurality of different treatment devices that are useable to deliver a surgical treatment via the trajectory path of the one or a selected one or more of the plurality of candidate trajectories, wherein each treatment device has associated electronically defined features such as one or more of shape, size, length and/or thickness.

16. A surgical planning system, comprising:
a workstation comprising a display; and
a computer system in communication with or at least partially onboard the workstation, wherein the computer system is configured to:
provide at least one image of a brain of a patient;
register a digital brain atlas to the at least one image;
accept user input to confirm and/or identify at least one target treatment region in the brain of the patient;
determine regions in the brain that are to be avoided; and
identify one candidate trajectory or a plurality of different candidate trajectories for providing a respective trajectory path from a location external to the patient to the at least one target treatment region as a surgical treatment path;
wherein the computer system is configured to identify the plurality of different candidate trajectories and provide the plurality of different candidate trajectories in a ranked order, and
wherein the ranked order is based, at least in part, on a distance each respective candidate trajectory resides from a respective closest one of the determined regions that are to be avoided.

17. A surgical planning system, comprising:
a workstation comprising a display; and
a computer system in communication with or at least partially onboard the workstation, wherein the computer system is configured to:
provide at least one image of a brain of a patient;
register a digital brain atlas to the at least one image;
accept user input to confirm and/or identify at least one target treatment region in the brain of the patient;
determine regions in the brain that are to be avoided; and
identify one candidate trajectory or a plurality of different candidate trajectories for providing a respective trajectory path from a location external to the patient to the at least one target treatment region as a surgical treatment path;
wherein the computer system is configured to identify the plurality of different candidate trajectories and provide the plurality of different candidate trajectories in a ranked order based, at least in part, on whether there is one or more single one of the different candidate trajectories that provides complete coverage inside a treatment radius of the at least one target treatment region.

18. The system of claim 17, wherein, if there is no single one of the plurality of different candidate trajectories that can provide the complete coverage, the computer system is configured to provide the plurality of different candidate trajectories in a ranked order, based, at least in part, on whether a single stereotactic frame is able to accommodate at least two of the plurality of different candidate trajectories and provide complete coverage of the at least one target treatment region and a distance each respective candidate trajectory resides from at least a closest one of the determined regions that are to be avoided.

19. The system of claim 18, wherein, if there is no single one of the different candidate trajectories that can provide the complete coverage and no single stereotactic frame that is able to accommodate the at least two of the plurality of different candidate trajectories to provide the complete coverage, the computer system is configured to provide the plurality of different candidate trajectories in a ranked order, based, at least in part, on two-stereotactic frame solutions having a lesser number of trajectories that provides the complete coverage of the at least one treatment region and based on a distance each respective candidate trajectory resides from at least a closest one of the determined regions that are to be avoided.

* * * * *

UNITED STATES PATENT AND TRADEMARK OFFICE
CERTIFICATE OF CORRECTION

PATENT NO. : 12,087,429 B2
APPLICATION NO. : 17/232429
DATED : September 10, 2024
INVENTOR(S) : Orr et al.

It is certified that error appears in the above-identified patent and that said Letters Patent is hereby corrected as shown below:

In the Specification

Column 7, Lines 50-51: Please correct "https://www.fh.com/product/waypoint-navigator-software" to read --https://www.fh.co.com/product/waypoint-navigator-software--

Column 7, Lines 55-56: Please correct "https: https://www.cortechslabs.com/products/neuroquant/#" to read --https://www.cortechslabs.com/products/neuroquant/#--

Column 19, Line 34: Please correct "System 390" to read --System390--

Signed and Sealed this
Tenth Day of December, 2024

Katherine Kelly Vidal
*Director of the United States Patent and Trademark Office*